US007674959B2

(12) United States Patent
Carozzi et al.

(10) Patent No.: US 7,674,959 B2
(45) Date of Patent: Mar. 9, 2010

(54) AXMI-027, AXMI-036 AND AXMI-038, A FAMILY OF DELTA-ENDOTOXIN GENES AND METHODS FOR THEIR USE

(75) Inventors: Nadine Carozzi, Raleigh, NC (US); Tracy Hargiss, Kernersville, NC (US); Michael G. Koziel, Raleigh, NC (US); Nicholas B. Duck, Apex, NC (US)

(73) Assignee: Athenix Corporation, Research Triangle Park, NC (US)

( * ) Notice: Subject to any disclaimer, the term of this patent is extended or adjusted under 35 U.S.C. 154(b) by 395 days.

(21) Appl. No.: 11/396,808

(22) Filed: Apr. 3, 2006

(65) Prior Publication Data

US 2006/0242732 A1   Oct. 26, 2006

Related U.S. Application Data

(60) Provisional application No. 60/667,442, filed on Apr. 1, 2005.

(51) Int. Cl.
*A01H 5/00* (2006.01)
*A01H 5/10* (2006.01)
*C12N 15/82* (2006.01)
*C12N 15/32* (2006.01)
*C12P 21/04* (2006.01)

(52) U.S. Cl. .................. 800/302; 536/23.71; 424/93.2; 424/93.4; 435/418; 435/71.1; 800/279

(58) Field of Classification Search .................. None
See application file for complete search history.

(56) References Cited

U.S. PATENT DOCUMENTS 6,071,877 A * 6/2000 Delecluse et al. ............. 514/12

FOREIGN PATENT DOCUMENTS

EP         1 471 145 A   10/2004
WO   WO 2004/074462 A    9/2004
WO   WO 2005/021585 A    3/2005

OTHER PUBLICATIONS van Frankenhuyzen et al, 2002, The *Bacillus thuringiensis* toxin specificity database, http://www.glfc.cfs.nrcan.gc.ca/bacillus, accessed May 6, 2008.*
de Maagd et al, 1999, Appl. Environ. Microbiol. 65:4369-4374.*
de Maagd et al (2001, Trends Genet. 17:193-199).*
Aaronson et al (2001, FEMS Microbiol. Lett. 195:1-8.*
Guo et al (2004, Proc. Natl. Acad. Sci. USA 101: 9205-9210).*
Tounsi et al, 2003, J. Appl. Microbiol. 95:23-28.*
GenBank Report for Accession No. AAF89668. Direct Submission on Jul. 15, 1999.
GenBank Report for Accession No. CAA67506. Direct Submission on Jul. 4, 1996.

* cited by examiner

*Primary Examiner*—Anne R Kubelik
(74) *Attorney, Agent, or Firm*—Alston & Bird LLP

(57) ABSTRACT

Compositions and methods for conferring pesticidal activity to bacteria, plants, plant cells, tissues and seeds are provided. Compositions comprising a coding sequence for a delta-endotoxin polypeptide are provided. The coding sequences can be used in DNA constructs or expression cassettes for transformation and expression in plants and bacteria. Compositions also comprise transformed bacteria, plants, plant cells, tissues, and seeds. In particular, isolated delta-endotoxin nucleic acid molecules are provided. Additionally, amino acid sequences corresponding to the polynucleotides are encompassed. In particular, the present invention provides for isolated nucleic acid molecules comprising nucleotide sequences encoding the amino acid sequence shown in SEQ ID NOS:2, 11 and 13, or the nucleotide sequences set forth in SEQ ID NOS:1, 10 and 12, as well as variants and fragments thereof.

14 Claims, 4 Drawing Sheets

```
              1                                                                50
   axmi027    ..........  ..........  ..........  ......MKNN  QTHFSDELTN
   axmi036    ..........  ..........  ..MGNFYFVM  KDNYDSLIKK  GMKFYMDQSN
   axmi038    MLECSEAMGI  DLNAPNIREA  LSMNNYFIGK  VLSGHHINNN  GNGNTLSRTA
   Cry11Aa1   ..........  ..........  ..........  ..........  ..........
   Cry11Ba1   ..........  ..........  ..........  ..........  ..........
   Cry18Aa1   ..MNNNFNGG  NNTGNNFTGN  TLSNGICTKK  NMKGTLSRTA
   Cry18Ba1   ..........  ..........  ..........  ......MNNN  GN..ALSRTA
   Cry18Ca1   ..........  ..........  ..MNNYFIGK  VLSGHHINNN  GNGNTLSRTA
   Cry2Aa1    ..........  ..........  ..........  ..........  ..........

51                                                               100
   axmi027    HIEIANYP..  ........NE  NQNNRENVSD  VPMDTSSISN  AGMMTEEFEI
   axmi036    YDYLSDNEK.  ....QEVIPN  PGRMFHNYSD  NPEIADSQEK  IFKILKKENL
   axmi038    LTPT......  ........NN  NVNRGDLVTN  ..GLTPIDNN  FIGSNGFIPR
   Cry11Aa1   ..........  ..........  ......MED   ....SSLDTL  SIVNETDFPL
   Cry11Ba1   ..........  ..........  ......MQN   ....NNFNTT  EINNMINFPM
   Cry18Aa1   IFSDGISDDL  ICCLDPIYNN  NDNNNDAICD  ELGLTPIDNN  TICSTDFTPI
   Cry18Ba1   LTPT......  ........NN  KVISGDLVTN  ..GLPPIDNN  IICSNGFMPI
   Cry18Ca1   LTPT......  ........NN  NVNRGDLVTN  ..GLTPIDNN  FIGSNGFIPR
   Cry2Aa1    ..........  ..........  ......MNN   .....VLNSG  RTTICDAYNV 101                                                              150
   axmi027    DSVLAPRSAE  TDEEKLYRAW  ENWEMQSADV  RFPAVVGTIG  TLLAKEIAKY
   axmi036    TKSEQQILAG  IDPNNNEVGP  FLVPIIAAPI  ILTPAMIQVG  QWLAGKAGKW
   axmi038    NVTRKDPFRK  RTTQEFIREW  TEWKEKSASL  FTAPIVGVIT  STLLEALKKL
   Cry11Aa1   YNNYTEPT..  IAP.......  ..........  .ALIAVAPIA  QYLATAIGKW
   Cry11Ba1   YNGRLEPS..  LAP.......  ..........  .ALIAVAPIA  KYLATALAKW
   Cry18Aa1   NVMRTDPFRK  KSTQELTREW  TEWKENSPSL  FTPAIVGVVT  SFLLQSLKKQ
   Cry18Ba1   NVTRKNPFRK  RTTQEFIREW  TEWKENSPSL  FTAPIVGVVT  STLLEALKKQ
   Cry18Ca1   NVTRKDPFRK  RTTQEFIREW  TEWKEKSASL  FTAPIVGVIT  STLLEALKKL
   Cry2Aa1    VAHDPFSFEH  KSLDTIQKEW  MEWKRTDHSL  YVAPVVGTVS  SFLLKKVGSL 151                                                              200
   axmi027    AGKKLLKTLF  GLLFPSN..D  TLTMEAILEA  TEEMMNRKLS  EAIRDRVTQE
   axmi036    LIGKALGKLK  GFLFPSNNDP  DAKLEEMRQE  LEEQFNRRLQ  NDKYQSLLAA
   axmi038    VAGRVLMSLT  NLLFPNN..S  TSTMEEILRA  TEQYIQEQLD  TVTWNRVSQE
   Cry11Aa1   AAKAAFSKVL  SLIFPGS..Q  PATMEKVRTE  VETLINQKLS  QDRVNILNAE
   Cry11Ba1   AVKQGFAKLK  SEIFPGN..T  PATMDKVRIE  VQTLLDQRLQ  DDRVKILEGE
   Cry18Aa1   ATSFLLKTLT  DLLFPNN..S  SLTMEEILRA  TEQYVQERLD  TDTANRVSQE
   Cry18Ba1   VQSRLLLLMT  NLLFPNN..S  TSTMEEILRA  TEQYVQEQLD  TVTWNRVSQE
   Cry18Ca1   VAGRVLMSLT  NLLFPNN..S  TSTMEEILRA  TEQYIQEQLD  TVTWNRVSQE
   Cry2Aa1    IGKRILSELW  GIIFPSG..S  TNLMQDILRE  TEQFLNQRLN  TDTLARVNAE 201                                                              250
   axmi027    LKGLQNGITN  FLEDVEDFET  YASMSLERQK  LYRFKTNNPN  IEPKAIIDSI
   axmi036    YASILDAANE  FLYWANKVER  AEEAFARDNS  ..ESNKKTLE  DTKADTAGAF
   axmi038    LEGLKNDLRT  FNDQIDDFL.  ..........  .....QNRVG  ISPLAIIDSI
   Cry11Aa1   YRGIIEVSDV  FDAYIK....  ..........  .......QPG  FTPATAKGYF
   Cry11Ba1   YKGIIDVSKV  FTDYVN....  ..........  .......QSK  FETGTANRLF
   Cry18Aa1   LVGLKNNLTT  FNDQVEDFL.  ..........  .....QNRVG  ISPLAIIDSI
   Cry18Ba1   LEGLKNNLRT  FNDQIDDFL.  ..........  .....QNRVE  ISPTAMIDSI
   Cry18Ca1   LEGLKNDLRT  FNDQIDDFL.  ..........  .....QNRVG  ISPLAIIDSI
   Cry2Aa1    LIGLQANIRE  FNQQVDNFL.  ..........  .....NPTQN  PVPLSITSSV
```

FIG. 1A

```
             251                                                        300
axmi027   NEMNQTFDNR  MPQFTSDYPE  WKVELLPLFA  QAANLHLVFL  RDVVKNATDW
axmi036   RAVNTVAISW  INQCLVPG..  YEEITLPLFT  QMCTVHLTHL  KDGVLKGADW
axmi038   NTMQQLFVNR  LPQFQVSD..  DQVLLLPLFA  QAVTLHLTFV  RDIIINADEW
Cry11Aa1  LNLSGAIIQR  LPQFEVQT..  YEGVSIALFT  QMCTLHLTLL  KDGILAGSAW
Cry11Ba1  FDTSNQLISR  LPQFEIAG..  YEGVSISLFT  QMCTFHLGLL  KDGILAGSDW
Cry18Aa1  NTMQQLFVNR  LPQFQVSG..  YQVLLLPLFA  QAATLHLTFL  RDVIINADEW
Cry18Ba1  NTMQQVFVNR  LPQFQLSD..  YQLLLLPLFA  QGATLHLTFI  RDIIINAGEW
Cry18Ca1  NTMQQLFVNR  LPQFQVSD..  DQVLLLPLFA  QAVTLHLTFV  RDIIINADEW
Cry2Aa1   NTMQQLFLNR  LPQFQIQG..  YQLLLLPLFA  QAANMHLSFI  RDVILNADEW 301                                                        350
axmi027   GLTDANIVRY  TDRLKARVKE  YSNYALQTYK  EAFENMY..Y  SNGKVIPALD
axmi036   GLDPKDVDSY  RSIFHNNVNK  YTQQAITSFQ  AGFNRIASQN  NNTNLSAAYN
axmi038   NIPEAQLNTY  KRYLKQYVAQ  YSNYALSTYE  EAFRARF..Y  PRNTVENMLQ
Cry11Aa1  GFTQADVDSF  IKLFNQKVLD  YRTRLMRMYT  EEFGR....L  CKVSLKDGLT
Cry11Ba1  GFAPADKDAL  ICQFNRFVNE  YNTRLMVLYS  KEFGR....L  LAKNLNEALN
Cry18Aa1  NIPTAQLNTY  TRYFKEYIAE  YSNYALSTYD  DGFRTRF..Y  PRNTLEDMLQ
Cry18Ba1  NIPEAQLNTC  KRYLKQYVAQ  YSNYALSTYE  GAFRARF..Y  PRATLENMLQ
Cry18Ca1  NIPEAQLNTY  KRYLKQYVAQ  YSNYALSTYE  EAFRARF..Y  PRNTVENMLE
Cry2Aa1   GISAATLRTY  RDYLRNYTRD  YSNYCINTYQ  TAFRG.....  LNTRLHDMLE 351                                                        400
axmi027   FRNFMVFNVL  DYVSTWSMLR  YEGIIINSST  NVYSYLKNLE  VSVLPSAPSW
axmi036   YRAAMQVYAF  DYIYKWSFLR  YEGIEPEVSR  TLFYSTGVPK  FHEP....FT
axmi038   FKTFMTINVL  DFVSIWSLLK  YVNLYVSTSA  NLYNIGDNKV  NEGEYSISYW
Cry11Aa1  FRNMCNLYVF  PFAEAWSLMR  YEGLKLQSSL  SLWDYVGVSI  P.....VNYN
Cry11Ba1  FRNMCSLYVF  PFSEAWSLLR  YEGTKLENTL  SLWNFVGESI  NN....ISPN
Cry18Aa1  FKTFMTLNAL  DLVSIWSLLK  YVNLYVSTSA  NLYNIGDNKV  NEGAYPISYG
Cry18Ba1  FKTFMTLNVL  DLVSIWSLLK  YMNLYISTSA  NLYNIGDNKV  NEGEYSISYW
Cry18Ca1  FKTFMTLNVL  DLVSMWSLLK  YVNLYVSTSA  NLYNIGDNKV  NEGEYSISYW
Cry2Aa1   FRTYMFLNVF  EYVSIWSLFK  YQSLMVSSGA  NLYASGSGPQ  QTQSFTAQNW 401                                                        450
axmi027   SVLNQFLQGK  PFKIFSGLSS  RAYKQIEDGF  PSHGVTFKNY  NEIDSVRTHY
axmi036   ..HEHVYRTL  VGLPNTRIRG  VSVGYDVS..  ..ASKIQWPL  TGVRNHVLPL
axmi038   PFFNSYIQTR  ANYVLSGVSG  YAIRWTYNN.  ..PIFGRYIQ  DRLNNITASY
Cry11Aa1  EWGGLVYKLL  MGEVNQRLTT  VKFNYSFTN.  ..EPADIPAR  ENIRGVHPIY
Cry11Ba1  DWKGALYKLL  MGAPNQRLNN  VKFNYSYFS.  ..DTQATIHR  ENIHGVLPTY
Cry18Aa1  PFFNSYIQTK  SNYVLSGVSG  IGARFTYS..  ..TVLGRYLH  DDLKNIITTY
Cry18Ba1  PFFNSYIQTK  SNYVLSGVSG  YAIRWYYLN.  ..TFFGEYIQ  DNLYNIIASY
Cry18Ca1  PFFNTYIQTK  SNYVLSGVSG  YAMRWSYTN.  ..PFFGEYIQ  DHLYNITASY
Cry2Aa1   PFLYSLFQVN  SNYILSGISG  TRLSITFPNI  .GGLPGSTTT  HSLNSARVNY 451                                                        500
axmi027   KGG.......  ..........  ..SYIGPFGR  QDTPRSGS..  ....VYLVEF
axmi036   SGG.......  ..........  ..DYRAEFGN  LNAGLIGN..  ..........
axmi038   IGG.......  VNG.......  .PQIGQQLST  TELDQLVQ.Q  QARADIPVDF
Cry11Aa1  DPSSGLTGWI  GNGRTNNFNF  ADNNGNEIME  VRTQTFYQNP  ..NNEPIAPR
Cry11Ba1  NGGPTITGWI  GNGRFSGLSF  PCSNELEITK  IKQEITYNDK  GGNFNSIVPA
Cry18Aa1  VGG.......  TQG.......  .PNIGVQLST  TELDELKKQQ  QATRDSLVDF
Cry18Ba1  VGG.......  VNG.......  .PKIGVQLST  TELDKQIK.Q  QARAGMPTGL
Cry18Ca1  IGG.......  VNG.......  .PQIGQQLST  TELDQLVQ.Q  QARADIPVDF
Cry2Aa1   SGG.......  ..........  ..VSSGLIGA  TNLNHNFN..  ..........C
```

FIG. 1B

```
           501                                                             550
axmi027    ENYNKSFTLS NPIDNPITRI KQQKHYQK.. .DQIREVSQD ILIYEPGGSL
axmi036    ....YTFKTD PAQYEKSLHG QLLIRSDNGN TRWITYIDGT LLVGTGQFTG
axmi038    TQIPINCTLR NPLEVPYYAT RFNELTSLGT AGVGGFVRSD VFISNDSVCG
Cry11Aa1   DIINQILTAP AP..ADLFFK NADINVKFTQ WFQSTLYGWN IKLGTQTVLS
Cry11Ba1   ATRNEILTAT VPTSADPFFK TADINWKY.. FSPGLYSGWN IKFDDTVTLK
Cry18Aa1   QFFTLNCMLP NPITAPYFAT SLYESRYS.. .SIGGYLRKD VFKSEDSTCG
Cry18Ba1   DDLSFNCTLR NPTTVPYFAC NFQELTSSGT AGTGGFIRSD VFRSEDNICG
Cry18Ca1   TQIPINCTLR NPLEVPYYAT RFNELTSLGT AGVGGFVRSD VFISNDSVCG
Cry2Aa1    S......TVL PPLSTPFVRS WLDSGTDREG VATSTNWQTE SFQTTLSLRC 551                                                             600
axmi027    TNNS...GGY WSSYPDYTVK HVIGLPWMGV PTTNIPLLTH TG..SIVLPP
axmi036    TAFN...... .MHQPDHFIR TVAAITKMTN ...NTWYPII PLRGYPTGVD
axmi038    LGTN..YSSG QTFYPDYYIT NISATVQVNG TNTDISPLYF GENRAITSTN
Cry11Aa1   SRTG.TIPPN YLAYDGYYIR AISACPRGVS LAYNHDLTTL TYNRIEYDSP
Cry11Ba1   SRVPSIIPSN ILKYDDYYIR AVSACPKGVS LAYNHDFLTL TYNKLEYDAP
Cry18Aa1   LGNP..G..A WTSYPDYYIT NISATVQING ENTDTTPLYF KENRPITSTR
Cry18Ba1   LGTG..YASA WTSYPDYYIT NISATVQVDG INIDITPLCF GEDRAITSTH
Cry18Ca1   LGTN..YSSG QTFYPDYYIT NISATVQVNG TNTDISPLYF GENRAITSTN
Cry2Aa1    GAFSARG..N SNYFPDYFIR NISGVPLVIR NEDLTRPLHY NQIRNIESPS 601                                                             650
axmi027    RFPDT...SV VATFSRTQIA PYTHLSNYTF KHAVPNDGAG FTISPLQFTN
axmi036    AEN......I VAGLAPNNVQ NFMATNK... ..HKIPYDKS YTIPALHYSK
axmi038    GVN.....KV IAIYNRKTNY DDFTNIRGTI VHEAPTDSTG FTISPLHLDT
Cry11Aa1   TTE.....NI IVGFAPDNTK DFYSKKS... .HYLSETNDS YVIPALQFAE
Cry11Ba1   TTQ.....NI IVGFSPDNTK SFYRSNS... .HYLSTTDDA YVIPALQFST
Cry18Aa1   GVN.....KV IAVYNRKANI AG.TNQNGTM IHQAPPDGTG FTVSPLHPSA
Cry18Ba1   GVN.....KV IAVYNRKANI AG.TNQNGTM IHQAPNDGTG FTVSPLHLAS
Cry18Ca1   GVN.....KV IAIYNRKTNY DDFTNIRGTI VHEAPTDSTG FTISPLHLDT
Cry2Aa1    GTPGGARAYL VSVHNRKNNI YA.ANENGTM IHLAPEDYTG FTISPIHATQ 651                                                             700
axmi027    LSGFNAEKAY LRELFGNHGD GVVFPETRDT SVTYQYTIYN PTSTTRQYRI
axmi036    MSSETSGN.S FLYDEIANGA DGALRMKHGA TTVDYNLDIS GINRSTRYKI
axmi038    VNINSYL..Y IQENYGNNG. ....DSLRVI N.RAIIKYRL SAARSVIYRL
Cry11Aa1   VSDRSFL..E DTPDQATDGS IKFARTFISN EAKYSIRLNT GFNTATRYKL
Cry11Ba1   VSDRSFL..E DTPDQATDGS IKFTDTVLGN EAKYSIRLNT GFNTATRYRL
Cry18Aa1   NTITS....Y IKENYGNSG. ....DSLHLK G.QGYLHYML SGNGQDRYRL
Cry18Ba1   FTHPSEA..H IQENYGNSG. ....DSLRLT GPTTAITYML SGDGRTIYKL
Cry18Ca1   VNINSYL..Y IQENYGNNG. ....DSLRVI N.RAIIKYRL SAARSVIYRL
Cry2Aa1    VNNQTRT..F ISEKFGNQG. ....DSLRFE QSNTTARYTL RGNG.NSYNL 701                                                             750
axmi027    YLKLATPNGP AKFWLQFHGE GSVRYDVDTR DLNDGINDNG ATFHEKHYNT
axmi036    FIRVKDG.ST GFEVKLVNDP RTSFNFHPIS SHTGEAGYTD YLSDSFNFSN
axmi038    VLRVSGTASS IVAIYE.NYP VGSANQINTG TDNEGVIDND SKFIDLIFNT
Cry11Aa1   IIRVRVPYRL PAGIRVQSQN SGNNRMLGSF TANANPEWVD FVTDAFTFND
Cry11Ba1   IIRFKAPARL AAGIRVRSQN SGNNKLLGGI PVEGNSGWID YITDSFTFDD
Cry18Aa1   VLRLSGAANQ IKLQS....P TTSIYAFDTS TNNEGITDNG SKFKDFAFST
Cry18Ba1   VLRVSGVITR ITAKVR.GNS IGYLEYINTV DNNQGITDNG SKFQDFEFRP
Cry18Ca1   VLRVSGTASS IVAIYE.NYP VGSANQINTG TDNEGVIDND SKFIDLIFNT
Cry2Aa1    YLRVSSIGNS TIRVTING.R VYTVSNVNTT TNNDGVNDNG ARFSDINIGN
```

FIG. 1C

```
         751                                                     800
axmi027  ITIPAGEH..  ...YVLGLEHQ  GPAAILGRIM  LTPTNVTPIY  ..........
axmi036  SNEILRITR.  ......NNSD   TNDLWFNQII  IVLETTFEQS  M.........
axmi038  PFSVSGTARE  LQLQVSGATT   SSPLDIMNII  LIPINDVPL.  ..........
Cry11Aa1 LGITTSSTNA  LFSISSDSLN   SGEEWYLSQL  FLVKESAFTT  QINPLLK...
Cry11Ba1 LGITTSSTNA  FFSIDSDGVN   ASQQWYLSKL  ILVKESSFTT  QIPLKPYVIV
Cry18Aa1 PFVIPEQK..  ...EIVLYFEG  VGSLDLMNLI  FLPADDTPLY  ..........
Cry18Ba1 TITIDAQT..  ...PIVLEFSA  TSNFDLMNLI  FIPYYDTPIY  ..........
Cry18Ca1 PFSVSGTARE  LQLQVSGATT   SSPLDIMNII  LIPINDVPLY  ..........
Cry2Aa1  IVASDNTN.V  TLDINVTLNS   GTPFDLMNIM  FVPTNLPPLY  ..........

801                                                     850
axmi027  ..........  ..........  ..........  ..........  ..........
axmi036  ..........  ..........  ..........  ..........  ..........
axmi038  ..........  ..........  ..........  ..........  ..........
Cry11Aa1 ..........  ..........  ..........  ..........  ..........
Cry11Ba1 RCPDTFFVSN  NSSSTYEQGY  NNNYNQNSSS  MYDQGYNNSY  NPNSGCTCNQ
Cry18Aa1 ..........  ..........  ..........  ..........  ..........
Cry18Ba1 ..........  ..........  ..........  ..........  ..........
Cry18Ca1 ..........  ..........  ..........  ..........  ..........
Cry2Aa1  ..........  ..........  ..........  ..........  ..........

851             874
axmi027  ..........  ..........  ....
axmi036  ..........  ..........  ....
axmi038  ..........  ..........  ....
Cry11Aa1 ..........  ..........  ....
Cry11Ba1 DYNNSYNQNS  GCTCNQGYNN  NYPK
Cry18Aa1 ..........  ..........  ....
Cry18Ba1 ..........  ..........  ....
Cry18Ca1 ..........  ..........  ....
Cry2Aa1  ..........  ..........  ....
```

FIG. 1D

AXMI-027, AXMI-036 AND AXMI-038, A FAMILY OF DELTA-ENDOTOXIN GENES AND METHODS FOR THEIR USE

CROSS REFERENCE TO RELATED APPLICATION

This application claims the benefit of U.S. Provisional Application Ser. No. 60/667,442, filed Apr. 1, 2005, the contents of which are hereby incorporated in their entirety by reference herein.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Dipteran, and Coleopteran larvae. These proteins also have shown activity against *Hymenoptera, Homoptera*, Phthiraptera, Mallophaga, and Acari pest orders, as well as other invertebrate orders such as Nemathelminthes, Platyhelminthes, and Sarcomastigorphora (Feitelson (1993) "The *Bacillus Thuringiensis* family tree" in *Advanced Engineered Pesticides* (Marcel Dekker, Inc., New York)) These proteins were originally classified as CryI to CryV based primarily on their insecticidal activity. The major classes were *Lepidoptera*-specific (I), *Lepidoptera*- and *Diptera*-specific (II), *Coleoptera*-specific (III), *Diptera*-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in 'jelly-roll' formation (de Maagd et al., 2001, supra). Domains II and III are involved in receptor recognition and binding, and are therefore considered determinants of toxin specificity.

Because of the devastation that insects can confer there is a continual need to discover new forms of *Bacillus thuringiensis* delta-endotoxins.

SUMMARY OF INVENTION

Compositions and methods for conferring insect pest resistance to bacteria, plants, plant cells, tissues and seeds are provided. Compositions include nucleic acid molecules encoding sequences for delta-endotoxin polypeptides, vectors comprising those nucleic acid molecules, and host cells comprising the vectors. Compositions also include the polypeptide sequences of the endotoxin, and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated nucleic acid molecules corresponding to delta-endotoxin nucleic acid sequences are provided. Additionally, amino acid sequences corresponding to the polynucleotides are encompassed. In particular, the present invention provides for an isolated nucleic acid molecule comprising a nucleotide sequence encoding the amino acid sequence shown in SEQ ID NO:2, a nucleotide sequence set forth in SEQ ID NO:1, or the delta-endotoxin nucleotide sequence deposited in a bacterial host as Accession No. NRRL B-30818, as well as variants and fragments thereof. Nucleotide sequences that are complementary to a nucleotide sequence of the invention, or that hybridize to a sequence of the invention are also encompassed.

Methods are provided for producing the polypeptides of the invention, and for using those polypeptides for controlling or killing a lepidopteran, heteropteran or coleopteran pest. Methods and kits for detecting the nucleic acids and polypeptides of the invention in a sample are also included.

The compositions and methods of the invention are useful for the production of organisms with insect pest resistance, specifically bacteria and plants. These organisms and the compositions derived from them are desirable for agricultural purposes. The compositions of the invention are also useful for generating altered or improved delta-endotoxin proteins that have pesticidal activity, or for detecting the presence of delta-endotoxin proteins or nucleic acids in products or organisms.

DESCRIPTION OF FIGURES

FIG. 1 shows an alignment of AXMI-027 (SEQ ID NO:2), AXMI-036 (SEQ ID NO:11) and AXMI-038 (SEQ ID NO:13) with cry11Aa (SEQ ID NO:14), cry11Ba (SEQ ID NO:15), cry18Aa (SEQ ID NO:3), cry18Ba (SEQ ID NO:4), cry18Ca (SEQ ID NO:5), and cry2Aa (SEQ ID NO:6). Toxins having C-terminal non-toxic domains were artificially truncated as shown. Conserved group 1 is found from about amino acid residue 223 to about 252 of SEQ ID NO:2. Conserved group 2 is found from about amino acid residue 301 to about 318 of SEQ ID NO:2. Conserved group 4 is found from about amino acid residue 610 to about 621 of SEQ ID NO:2. Conserved group 5 is found from about amino acid residue 684 to about 693 of SEQ ID NO:2.

DETAILED DESCRIPTION

The present invention is drawn to compositions and methods for regulating pest resistance in organisms, particularly plants or plant cells. The methods involve transforming organisms with a nucleotide sequence encoding a delta-endotoxin protein of the invention. In particular, the nucleotide sequences of the invention are useful for preparing plants and microorganisms that possess pesticidal activity. Thus, transformed bacteria, plants, plant cells, plant tissues and seeds are provided. Compositions are delta-endotoxin nucleic acids and proteins of *Bacillus thuringiensis*. The sequences find use in the construction of expression vectors for subsequent transformation into organisms of interest, as probes for the isolation of other delta-endotoxin genes, and for the generation of altered pesticidal proteins by methods known in the art, such as domain swapping or DNA shuffling. The proteins find use in controlling or killing lepidopteran, heteropteran or coleopteran pest populations and for producing compositions with pesticidal activity.

A plasmid containing the insect pest resistance nucleotide sequence of the invention was deposited in the permanent collection of the Agricultural Research Service Culture Collection, Northern Regional Research Laboratory (NRRL), 1815 North University Street, Peoria, Ill. 61604, United States of America, on Feb. 8, 2005, and assigned Accession No. NRRL B-30818 (for AXMI-027). This deposit will be maintained under the terms of the Budapest Treaty on the International Recognition of the Deposit of Microorganisms for the Purposes of Patent Procedure. Access to this deposit will be available during the pendency of the application to the Commissioner of Patents and Trademarks and persons determined by the Commissioner to be entitled thereto upon request. Upon allowance of any claims in the application, the Applicants will make available to the public, pursuant to 37 C.F.R. § 1.808, sample(s) of the deposit with the NRRL. This deposit was made merely as a convenience for those of skill in the art and is not an admission that a deposit is required under 35 U.S.C. §112.

By "delta-endotoxin" is intended a toxin from *Bacillus thuringiensis* that has toxic activity against one or more pests, including, but not limited to, members of the *Lepidoptera, Diptera*, and *Coleoptera* orders, or a protein that has homology to such a protein. In some cases, delta-endotoxin proteins have been isolated from other organisms, including *Clostridium bifermentans* and *Paenibacillus popilliae*. Delta-endotoxin proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein. Delta-endotoxins include proteins identified as cry1 through cry43, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiensis* toxin nomenclature," available at the University of Sussex, School of Life Sciences website on the World Wide Web.

Provided herein are novel isolated nucleotide sequences that confer pesticidal activity. Also provided are the amino acid sequences of the delta-endotoxin proteins. The protein resulting from translation of this gene allows cells to control or kill pests that ingest it.

Isolated Nucleic Acid Molecules, and Variants and Fragments Thereof

One aspect of the invention pertains to isolated nucleic acid molecules comprising nucleotide sequences encoding delta-endotoxin proteins and polypeptides or biologically active portions thereof, as well as nucleic acid molecules sufficient for use as hybridization probes to identify delta-endotoxin encoding nucleic acids. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include the sequences set forth in SEQ ID NOS:1, 10 and 12, the delta endotoxin nucleotide sequence deposited in a bacterial host as Accession No. NRRL B-30818, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the delta-endotoxin protein encoded by these nucleotide sequences are set forth in SEQ ID NOS:2, 11 and 13.

Nucleic acid molecules that are fragments of these delta-endotoxin encoding nucleotide sequences are also encompassed by the present invention. By "fragment" is intended a portion of the nucleotide sequence encoding a delta-endotoxin protein. A fragment of a nucleotide sequence may encode a biologically active portion of a delta-endotoxin protein, or it may be a fragment that can be used as a hybridization probe or PCR primer using methods disclosed below.

Nucleic acid molecules that are fragments of a delta-endotoxin nucleotide sequence comprise at least about 50, 100, 200, 300, 400, 500, 600, 700, 800, 900, 1000, 1050, 1100, 1150, 1200, 1250, 1300, 1350, 1400, 1450, 1500, 1550, 1600, 1650, 1700, 1750, 1800, 1850, 1900, 1950, 2000, or 2050 contiguous nucleotides, or up to the number of nucleotides present in a full-length delta-endotoxin encoding nucleotide sequence disclosed herein (for example, 2050 nucleotides for SEQ ID NO:1, 2050 nucleotides for SEQ ID NO:10, 2151 nucleotides for SEQ ID NO:12) depending upon the intended use. By "contiguous" nucleotides is intended nucleotide residues that are immediately adjacent to one another. Fragments of the nucleotide sequences of the present invention will encode protein fragments that retain the biological activity of the delta-endotoxin protein and, hence, retain pesticidal activity. By "retains activity" is intended that the fragment will have at least about 30%, at least about 50%, at least about 70%, or at least about 80% of the pesticidal activity of the delta-endotoxin protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a delta-endotoxin encoding nucleotide sequence that encodes a biologically active portion of a protein of the invention will encode at least about 15, 25, 30, 50, 75, 100, 125, 150, 175, 200, 250, 300, 350, 400, 450, 500, 550, 600, or 650 contiguous amino acids, or up to the total number of amino acids present in a full-length delta-endotoxin protein of the invention (for example, 700 amino acids for SEQ ID NO:2, 685 amino acids for SEQ ID NO:11, 717 amino acids for SEQ ID NO:13).

Preferred delta-endotoxin proteins of the present invention are encoded by a nucleotide sequence sufficiently identical to the nucleotide sequence of SEQ ID NOS:1, 10 or 12. By "sufficiently identical" is intended an amino acid or nucleotide sequence that has at least about 60% or 65% sequence identity, preferably about 70% or 75% sequence identity, more preferably about 80% or 85% sequence identity, most preferably about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to delta-endotoxin-like nucleic acid molecules of the invention. BLAST protein searches can be performed with the BLASTX program, score=50, wordlength=3, to obtain amino acid sequences homologous to delta-endotoxin protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by visual inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

A preferred program is GAP version 10, which uses the algorithm of Needleman and Wunsch (1970) *J. Mol. Biol.* 48:443-453. GAP Version 10 may be used with the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 Scoring Matrix. Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by GAP Version 10.

The invention also encompasses variant nucleic acid molecules. "Variants" of the delta-endotoxin encoding nucleotide sequences include those sequences that encode the delta-endotoxin proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the delta-endotoxin proteins disclosed in the present invention as discussed below. Variant proteins encompassed by the present invention are biologically active, that is they continue to possess the desired biological activity of the native protein, that is, retaining pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation into the nucleotide sequences of the invention thereby leading to changes in the amino acid sequence of the encoded delta-endotoxin proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably conservative amino acid substitutions may be made at one or more predicted, preferably nonessential amino acid residues. A "nonessential" amino acid residue is a residue that can be altered from the wild-type sequence of a delta-endotoxin protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in 'jelly-roll' formation (de Maagd et al., 2001, supra). Domains II and III are involved in receptor recognition and binding, and are therefore considered determinants of toxin specificity. Conserved domains in the delta-endotoxin sequences of the invention can be identified, for example, by aligning the amino acid sequences of the invention with known delta-endotoxin amino acid sequences and identifying the conserved regions as taught by de Maagd, 2001, supra.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in the alignment of FIG. 1. Examples of residues that are conserved but that may allow conservative amino acid substitutions and still retain activity include, for example, residues that have only conservative substitutions between all proteins contained in the alignment of FIG. 1. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer delta-endotoxin activity to identify mutants that retain activity. Following mutagenesis, the encoded protein can be expressed recombinantly, and the activity of the protein can be determined using standard assay techniques.

Using methods such as PCR, hybridization, and the like corresponding delta-endotoxin sequences can be identified, such sequences having substantial identity to the sequences of the invention. See, for example, Sambrook J., and Russell, D. W. (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the delta-endotoxin nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known delta-endotoxin-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, preferably about 25, more preferably at least about 50, 75, 100, 125, 150, 175, 200, 250, 300, 350, or 400 consecutive nucleotides of delta-endotoxin encoding nucleotide sequence of the invention or a fragment or variant thereof. Methods for the preparation of probes for hybridization are generally known in the art and are disclosed in Sambrook and Russell, 2001, herein incorporated by reference.

For example, an entire delta-endotoxin sequence disclosed herein, or one or more portions thereof, may be used as a probe capable of specifically hybridizing to corresponding delta-endotoxin-like sequences and messenger RNAs. To achieve specific hybridization under a variety of conditions, such probes include sequences that are unique and are at least about 10 nucleotides in length, or at least about 20 nucleotides in length. Such probes may be used to amplify corresponding delta-endotoxin sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.$+16.6(\log M)+0.41(\% GC)-0.61(\% form)-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Delta-endotoxin proteins are also encompassed within the present invention. By "delta-endotoxin protein" is intended a protein having the amino acid sequence set forth in SEQ ID NOS:2, 11 or 13. Fragments, biologically active portions, and variants thereof are also provided, and may be used to practice the methods of the present invention.

"Fragments" or "biologically active portions" include polypeptide fragments comprising amino acid sequences sufficiently identical to the amino acid sequences set forth in SEQ ID NOS:2, 11, or 13, and that exhibit pesticidal activity. A biologically active portion of a delta-endotoxin protein can be a polypeptide that is, for example, 10, 25, 50, 100 or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:2. The invention encompasses other fragments, however, such as any fragment in the protein greater than about 10, 20, 30, 50, 100, 150, 200, 250, 300, 350, 400, 400, 450, 500, 550, 600, or 650 amino acids.

By "variants" is intended proteins or polypeptides having an amino acid sequence that is at least about 60%, 65%, preferably about 70%, 75%, more preferably 80%, 85%, most preferably 90%, 91%, 92%, 93%, 94%, 95%, 96%, 97%, 98% or 99% identical to the amino acid sequence of SEQ ID NOS:2, 11 or 13. Variants also include polypeptides encoded by a nucleic acid molecule that hybridizes to the nucleic acid molecule of SEQ ID NO:1, 10 or 12, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi-027, axmi-036, or axmi-038 genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may also lead to generation of delta-endotoxin proteins that encode pesticidal activity. These delta-endotoxin proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane, eds. (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a delta-endotoxin may be altered by various methods, and that these alterations may result in DNA sequences encoding proteins with amino acid sequences different than that encoded by a delta-endotoxin of the present invention. This protein may be altered in various ways including amino acid substitutions, deletions, truncations, and insertions. Methods for such manipulations are generally known in the art. For example, amino acid sequence variants of a delta-endotoxin protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a delta-endotoxin to confer pesticidal activity may be improved by the use of such techniques upon the compositions of this invention. For example, one may express a delta-endotoxin in host cells that exhibit high rates of base misincorporation during DNA replication, such as XL-1 Red (Stratagene, La Jolla, Calif.). After propagation in such strains, one can isolate the delta-endotoxin DNA (for example by preparing plasmid DNA, or by amplifying by PCR and cloning the resulting PCR fragment into a vector), culture the delta-endotoxin mutations in a non-mutagenic strain, and identify mutated delta-endotoxin genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest, (2) introduce a binding domain, enzymatic activity, or epitope to facilitate either protein purification, protein detection, or other experimental uses known in the art, or, (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different delta-endotoxin protein coding regions can be used to create a new delta-endotoxin protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a delta-endotoxin gene of the invention and other known delta-endotoxin genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered delta-endotoxin proteins. Domains II and III may be swapped between delta-endotoxin proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Micriobiol.* 65:2918-2925).

Vectors

A delta-endotoxin sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) Trends in Plant Science 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the delta-endotoxin sequence to be under the transcriptional regulation of the regulatory regions.

The expression cassette will include in the 5'-3' direction of transcription, a transcriptional and translational initiation region (i.e., a promoter), a DNA sequence of the invention, and a transcriptional and translational termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the delta-endotoxin is targeted to the chloroplast for expression. In this manner, where the delta-endotoxin is not directly inserted into the chloroplast, the expression cassette will additionally contain a nucleic acid encoding a transit peptide to direct the delta-endotoxin to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196: 1414-1421; and Shah et al. (1986) *Science* 233:478-481.

The delta-endotoxin gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

Transformation of plant cells can be accomplished by one of several techniques known in the art. The delta-endotoxin gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector." This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the delta-endotoxin are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Then molecular and biochemical methods will be used for confirming the presence of the integrated heterologous gene of interest in the genome of transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}P$ target DNA fragment to confirm the integration of introduced gene in the plant genome according to standard techniques (Sambrook and Russell, 2001, supra).

In Northern blot analysis, RNA is isolated from specific tissues of transformant, fractionated in a formaldehyde agarose gel, blotted onto a nylon filter according to standard procedures that are routinely used in the art (Sambrook and Russell, 2001, supra). Expression of RNA encoded by the delta-endotoxin is then tested by hybridizing the filter to a radioactive probe derived from a delta-endotoxin, by methods known in the art (Sambrook and Russell, 2001, supra).

Western blot and biochemical assays and the like may be carried out on the transgenic plants to confirm the presence of protein encoded by the delta-endotoxin gene by standard procedures (Sambrook and Russell, 2001, supra) using antibodies that bind to one or more epitopes present on the delta-endotoxin protein.

Pesticidal Activity in Plants

In another aspect of the invention, one may generate transgenic plants expressing a delta-endotoxin that has pesticidal activity. Methods described herein by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a delta-endotoxin may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314, bromoxynil resistance nitrilase gene; and Sathasivan et al. (1990) *Nucl. Acids Res.* 18:2188, AHAS imidazolinone resistance gene).

Fertile plants expressing a delta-endotoxin may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Cucumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape., etc.).

Use in Pesticidal Control

General methods for employing strains comprising a nucleotide sequence of the present invention, or a variant thereof, in pesticide control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a delta-endotoxin gene into a cellular host. Expression of the delta-endotoxin gene results, directly or indirectly, in the intracellular production and maintenance of the pesticide. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscocides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be preparable by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, heteropteran or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Heteroptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

The order Heteroptera includes the families Miridae, Lygaeidae, Pentatomidae, Tingidae, Coreidae, Alydidae, Rhopalidae, and Rhopalidae.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm;

*Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carnine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carnine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

The following examples are offered by way of illustration and not by way of limitation.

EXPERIMENTAL

Example 1

Extraction of Plasmid DNA

A pure culture of strain ATX14819 was grown in large quantities of rich media. The culture was spun to harvest the cell pellet. The cell pellet was then prepared by treatment with SDS by methods known in the art, resulting in breakage of the cell wall and release of DNA. Proteins and large genomic DNA was then precipitated by a high salt concentration. The plasmid DNA was then precipitated by standard ethanol precipitation. The plasmid DNA was separated from any remaining chromosomal DNA by high-speed centrifugation through a cesium chloride gradient. The DNA was visualized in the gradient by UV light and the band of lower density (i.e. the lower band) was extracted using a syringe. This band contained the plasmid DNA from Strain ATX14819. The quality of the DNA was checked by visualization on an agarose gel.

Example 2

Cloning of Genes

The purified plasmid DNA was sheared into 5-10 kb sized fragments and the 5' and 3' single stranded overhangs repaired using T4 DNA polymerase and Klenow fragment in the presence of all four dNTPs. Phosphates were then attached to the 5' ends by treatment with T4 polynucleotide kinase. The repaired DNA fragments were then ligated overnight into a standard high copy vector (i.e. pBLUESCRIPT® SK+), suitably prepared to accept the inserts as known in the art (for example by digestion with a restriction enzyme producing blunt ends).

The quality of the library was analyzed by digesting a subset of clones with a restriction enzyme known to have a cleavage site flanking the cloning site. A high percentage of clones were determined to contain inserts, with an average insert size of 5-6 kb.

Example 3

High Throughput Sequencing of Library Plates

Once the shotgun library quality was checked and confirmed, colonies were grown in a rich broth in 2 ml 96-well blocks overnight at 37° C. at a shaking speed of 350 rpm. The blocks were spun to harvest the cells to the bottom of the block. The blocks were then prepared by standard alkaline lysis prep in a high throughput format.

The end sequences of clones from this library were then determined for a large number of clones from each block in the following way: The DNA sequence of each clone chosen for analysis was determined using the fluorescent dye terminator sequencing technique (Applied Biosystems) and standard primers flanking each side of the cloning site. Once the reactions had been carried out in the thermocycler, the DNA was precipitated using standard ethanol precipitation. The DNA was resuspended in water and loaded onto a capillary sequencing machine. Each library plate of DNA was sequenced from either end of the cloning site, yielding two reads per plate over each insert.

Example 4

Assembly and Screening of Sequencing Data

DNA sequences obtained were compiled into an assembly project and aligned together to form contigs. This can be done efficiently using a computer program, such as Vector NTi, or alternatively by using the Pred/Phrap suite of DNA alignment and analysis programs. These contigs, along with any individual read that may not have been added to a contig, were compared to a compiled database of all classes of known pesticidal genes. Contigs or individual reads identified as having identity to a known endotoxin or pesticidal gene were analyzed further. A single clone, pAX027, was found to contain DNA showing homology to known endotoxin genes. Therefore, pAX027 was selected for further sequencing.

Example 5

Sequencing of pAX027, and Identification of AXMI-027

Primers were designed to anneal to pAX027, in a manner such that DNA sequences generated from such primers will overlap existing DNA sequence of this clone(s). This process, known as "oligo walking", is well known in the art. This process was utilized to determine the entire DNA sequence of the region exhibiting homology to a known endotoxin gene. In the case of pAX027, this process was used to determine the DNA sequence of the entire clone, resulting in a single nucleotide sequence. The completed DNA sequence was then placed back into the original large assembly for further validation. This allowed incorporation of more DNA sequence reads into the contig, resulting in 6-7 reads of coverage over the entire region.

Analysis of the DNA sequence of pAX027 by methods known in the art identified an open reading frame consisting of 2100 nucleotides and 700 amino acids, with homology to known delta endotoxin genes. This open reading frame is designated as AXMI-027. The DNA sequence of AXMI-027 is provided as SEQ ID NO:1 and the amino acid sequence of the predicted AXMI-27 protein is provided in SEQ ID NO:2.

Example 6

Homology of AXMI-027 to Known Endotoxin Genes

Searches of DNA and protein databases with the DNA sequence and amino acid sequence of AXMI-027 reveal that AXMI-027 is homologous to known endotoxins. Blast searches identify cry18Aa protein (Accession No. CAA67506) as having the strongest block of homology, with an overall sequence identity in the toxic domain of 26% (see Table 1).

FIG. 1 shows an alignment of AXMI-027 (SEQ ID NO:2) with the highest scoring proteins identified by Blast search. AXMI-027 appears to be a naturally truncated delta-endotoxin, containing only the toxic N-terminal domains. All of the Blast hits were also naturally truncated genes except for cry26Aa(*), which was artificially truncated at its predicted cleavage site.

TABLE 1

Amino Acid Identity of AXMI-027 with Exemplary Endotoxin Classes

| Endotoxin | Percent Amino Acid Identity to AXMI-027 | Percent Amino Acid Identity in Toxic Domains |
|---|---|---|
| cry18Aa | 26% | 26% |
| cry18Ba | 25% | 25% |
| cry18Ca | 26% | 26% |
| cry2Aa | 24% | 24% |
| cry2Ab | 24% | 24% |
| cry2Ac | 23% | 23% |
| cry26Aa* | 11% | 14% |

Searches of the pFAM database identify AXMI-027 as having homology to the delta endotoxin, N-terminal domain family (PFAM Accession No. PF03945). An Endotoxin_N domain is found between amino acid residues 90 and 323 of AXMI-027 (SEQ ID NO:2).

This family contains insecticidal toxins produced by Bacillus species of bacteria. The N terminus of the crystalized protein is cleaved after insect ingestion, resulting in an activated protein. The C terminal extension is cleaved in some protein members. This activated region of the delta endotoxin is composed of three structural domains. The N-terminal helical domain is involved in membrane insertion and pore formation. The second and third domains are involved in receptor binding.

Example 7

Cloning of AXMI-027 for Protein Expression

AXMI-027 is cloned into a vector for *E. coli* expression as follows. pAX998 contains the ampicillin resistance gene for selection of transformants, and the tac promoter which is inducible by IPTG for regulated protein expression. pAX998 also has a 6×His tag region immediately upstream of the insert cloning region, such that any resulting clones would contain a 6×His tag at the N-terminus of the expressed protein. Methods for expressing proteins with 6×His tag fusions, and their use for purification and analysis of protein expression are well known in the art.

The coding sequence for AXMI-027 is PCR-amplified using PFUULTRA™ High-Fidelity DNA Polymerase (Stratagene). Oligonucleotide primers are designed such that the resulting PCR product contains desired restriction sites near each end, to facilitate cloning. The resulting PCR product (approximately 2.2 kb) is digested with the appropriate restriction enzyme, and subcloned into the E. coli expression vector, pAX997. Insert-containing clones are identified by restriction analysis. The resulting clone, pAX965, contains the AXMI-027 open reading frame fused to the 6×His tag, such that transcription and translation result in production of a "fusion protein" with a stretch of six histidines. The DNA sequence of pAX965 is confirmed by DNA sequence analysis and is subsequently transformed into chemically competent E. coli BL21, as described by the manufacturer (Stratagene, La Jolla, Calif.).

A single colony of pAX965 in BL21 is inoculated into LB media supplemented with ampicillin and grown for several hours at 37° C. with vigorous agitation. These cultures are diluted into fresh LB media at a 1:50 dilution, then grown to an $OD_{600}$ ranging from 0.6-0.8. The protein production is induced by addition of 0.1 mM IPTG and cultures are grown under inducing conditions overnight at 20° C. The cells are then pelleted by centrifugation and resuspended in PBS. Cells are sonicated for a total of 30 seconds using 10-second sonication intervals and incubated on ice for one minute.

Example 8

Expression of AXMI-027 in Bacillus

The insecticidal AXMI-027 gene is amplified by PCR from pAX027, and cloned into the Bacillus Expression vector pAX916 by methods well known in the art. The Bacillus strain containing the vector with AXMI-027, pAX967, may be cultured on a variety of conventional growth media. A Bacillus strain containing pAX931 is grown in CYS media (10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$), until sporulation is evident by microscopic examination. Samples are prepared, and AXMI-027 is tested for insecticidal activity in bioassays against important insect pests.

Example 9

Expression of AXMI-036 in Bacillus

The insecticidal axmi-036 gene was identified in a DNA library from strain ATX14759, in plasmid pATX147599010H12. The open reading frame was amplified by PCR from plasmid pATX147599010H12 and cloned into the Bacillus expression vector pAX916 by methods well known in the art to create the plasmid pAX2567. The Bacillus strain containing pAX$^2$567 may be cultured on a variety of conventional growth media. A Bacillus strain containing pAX2567 was grown in CYS media (10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$, 7 g/l glucose), until sporulation and lysis were evident by microscopic examination. Samples were prepared from these sporulated cultures for bioassay testing.

To prepare CYS media: 10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$. The CYS mix should be pH 7, if adjustment is necessary. NaOH or HCl are preferred. The media is then autoclaved and 100 ml of 10× filtered glucose is added after autoclaving. If the resultant solution is cloudy it can be stirred at room temperature to clear.

Example 10

Cloning of axmi-038 from Paenibacillus popilliae axmi-038 was amplified as two overlapping PCR fragments from strain ATX21738 (Paenibacillus popilliae) and assembled into a single DNA clone by virtue of a shared Nsp I restriction enzyme site as known in the art to yield plasmid pAX2003. The DNA sequence of the resulting clone was determined by methods known in the art.

Example 11

Homology of AXMI-027, AXMI-036, and AXMI-038 to Known Genes

The amino acid sequences of AXMI-027, AXMI-036, and AXMI-038 were compared to public databases, such as GENBANK®, and the proteins with closest amino acid homology determined. These proteins were then aligned with the amino acid sequences of the closest homologues and the following percent identity was determined.

TABLE 2

| Amino acid identity to known proteins | | |
|---|---|---|
| Protein | Closest Homolog | % Identity |
| AXMI-027 | Cry18Ca1 | 27.0% |
| AXMI-036 | Cry11Ba1 | 21.5% |
| AXMI-038 | Cry18Ca1 | 95.0% |

Example 12

Assay for Pesticidal Activity

The ability of a pesticidal protein to act as a pesticide upon a pest is often assessed in a number of ways. One way well known in the art is to perform a feeding assay. In such a feeding assay, one exposes the pest to a sample containing either compounds to be tested, or control samples. Often this assay is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) *Pesticide bioassays with arthropods* (CRC, Boca Raton, Fla.). Alternatively, assays are commonly described in the journals *Arthropod Management Tests and Journal of Economic Entomology* or by discussion with members of the Entomological Society of America (ESA).

Example 13

Insecticidal Activity of AXMI-036 on *Lygus lineolaris*

Cell-free protein extracts were prepared as follows. The *Bacillus* strain harboring pAX2567 was grown in 25 ml of CYS media for 9 days at 30 C. Eighteen ml of culture was then centrifuged at 8,600× g for ten minutes and the supernatant discarded. The pellet was resuspended in 20 ml of 20 mM Tris HCl at pH 8, centrifuged as above, and the supernatant discarded. The washed pellet was resuspended in 18 ml of 50 mM of sodium carbonate buffer (pH 10.5) containing 5 mM dithiothreitol, sonicated and incubated at room temperature for about 1.5 hours. The suspension was centrifuged as above and the supernatant was passed through a 0.2 μm filter. The filtrate contained approximately 350 μg of AXMI-036 protein per ml.

Bioassays were performed using multi well microtiter plates used as feeding chambers. The insecticidal protein or control was presented to the insect in a solution that was contained in pockets formed by a double layer of parafilm (Pechiney Plastic Packaging, Chicago Ill.) stamped on a template and sealed with a membrane (Research Products Int. Corp., Mt Prospect, Ill.) that the insect could pierce upon feeding. The sheet of parafilm containing the pockets was placed on top of the plate after $1^{st}$ or $2^{nd}$ instar Lygus nymphs were placed into individual wells with a fine tip brush. The sheet of parafilm acts as a seal containing the lygus within an individual well and also provides a feeding site. The resultant assay chamber was incubated at ambient temperature. Insecticidal proteins were mixed 1:1 with a commercially available liquid lygus diet (Bio Serv, Frenchtown, N.J.) and tested at a concentration of 175 vγ/μl.

TABLE 3

Insecticidal Activity of AXMI-036 on *Lygus lineolaris*

| Protein | No. Dead/Total | % Mortality |
|---|---|---|
| AXMI-036 | 10/17 | 60% |
| Control | 3/16 | 18% |

Example 14

Vectoring of axmi-027, axmi-036 and axmi-038 for Plant Expression

The axmi-027, axmi-036 or axmi-038 coding region DNA is operably connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter-gene-terminator constructs also are well known in the art.

The plant expression cassettes described above are combined with an appropriate plant selectable marker to aid in the selections of transformed cells and tissues, and ligated into plant transformation vectors. These may include binary vectors from *Agrobacterium*-mediated transformation or simple plasmid vectors for aerosol or biolistic transformation.

Example 15

Transformation of Maize Cells with axmi-027, axmi-036 and axmi-038

Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to express axmi-027, axmi-036 or axmi-038 in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

TABLE 3

| DN62A5S Media | | |
|---|---|---|
| Components | Per Liter | Source |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000 × Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |

TABLE 3-continued

DN62A5S Media

| Components | Per Liter | Source |
|---|---|---|
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 16

Transformation of axmi-027, axmi-036 and axmi-038 into Plant Cells by Agrobacterium-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessaryper se to incubate the embryos overnight. Embryos are contacted with an Agrobacterium strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising a nucleotide sequence selected from the group consisting of:
   a) the nucleotide sequence of SEQ ID NO: 10, or a complement thereof;
   b) a nucleotide sequence that encodes a polypeptide comprising the amino acid sequence of SEQ ID NO:11;
   c) a nucleotide sequence that encodes a polypeptide comprising an amino acid sequence having at least 95% sequence identity to the amino acid sequence of SEQ ID NO: 11, wherein said nucleotide sequence encodes a polypeptide having pesticidal activity towards Hemiptera pests; and
   d) the delta endotoxin nucleotide sequence of the DNA insert of the plasmid deposited as Accession No. NRRL B-30818, or complement thereof.

2. The isolated nucleic acid molecule of claim 1, wherein said nucleotide sequence is a synthetic sequence that has been designed for expression in a plant.

3. A vector comprising the nucleic acid molecule of claim 1.

4. The vector of claim 3, further comprising a nucleic acid molecule encoding a heterologous polypeptide.

5. A host cell that contains the vector of claim 3.

6. The host cell of claim 5 that is a bacterial host cell.

7. The host cell of claim 5 that is a plant cell.

8. A transgenic plant comprising the host cell of claim 7.

9. The transgenic plant of claim 8, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

10. A transformed seed comprising the nucleic acid sequence of claim 1.

11. A method for producing a polypeptide with pesticidal activity toward Hemiptera, said method comprising culturing a host cell comprising a vector comprising a nucleic acid molecule encoding said polypeptide, said polypeptide being selected from the group consisting of:
   a) a polypeptide comprising the amino acid sequence of SEQ ID NO: 11;
   b) a polypeptide comprising an amino acid sequence having at least 95% sequence identity to the amino acid sequence of SEQ ID NO: 11, wherein said polypeptide has pesticidal activity towards Hemiptera pests;
   c) a polypeptide that is encoded by the nucleotide sequence of SEQ ID NO:10; and
   d) a polypeptide encoded by the delta endotoxin nucleotide sequence of the DNA insert of the plasmid deposited as Accession No. NRRL B-30818.

12. A plant having stably incorporated into its genome a DNA construct comprising a nucleotide sequence that encodes a protein having pesticidal activity toward Hemiptera, wherein said nucleotide sequence is selected from the group consisting of:
   a) the nucleotide sequence of SEQ ID NO: 10, or a complement thereof
   b) a nucleotide sequence that encodes a polypeptide comprising the amino acid sequence of SEQ ID NO:11;
   c) a nucleotide sequence that encodes a polypeptide comprising an amino acid sequence having at least 95% sequence identity to the amino acid sequence of SEQ ID NO: 11, wherein said nucleotide sequence encodes a polypeptide having pesticidal activity towards Hemiptera pests; and
   d) the delta endotoxin nucleotide sequence of the DNA insert of the plasmid deposited as Accession No. NRRL B-30818, or complement thereof.

13. The plant of claim 12, wherein said plant is a plant cell.

14. A method for protecting a plant from a pest, said method comprising introducing into said plant or cell thereof at least one expression vector comprising a nucleotide sequence that encodes a pesticidal polypeptide toward Hemiptera, wherein said nucleotide sequence is selected from the group consisting of:
- a) the nucleotide sequence of SEQ ID NO: 10, or a complement thereof
- b) a nucleotide sequence that encodes a polypeptide comprising the amino acid sequence of SEQ ID NO:11;
- c) a nucleotide sequence that encodes a polypeptide comprising an amino acid sequence having at least 95% sequence identity to the amino acid sequence of SEQ ID NO: 11, wherein said nucleotide sequence encodes a polypeptide having pesticidal activity towards Hemiptera pests; and
- d) the delta endotoxin nucleotide sequence of the DNA insert of the plasmid deposited as Accession No. NRRL B-30818, or complement thereof.

* * * * *

SEQUENCE LISTING

<160> NUMBER OF SEQ ID NOS: 15

<210> SEQ ID NO 1
<211> LENGTH: 2100
<212> TYPE: DNA
<213> ORGANISM: Bacillus thuringiensis
<220> FEATURE:
<221> NAME/KEY: CDS
<222> LOCATION: (1)...(2100)

<400> SEQUENCE: 1

```
atg aaa aat aat caa aca cat ttt tcg gat gaa ttg act aat cat ata      48
Met Lys Asn Asn Gln Thr His Phe Ser Asp Glu Leu Thr Asn His Ile
 1               5                  10                  15 gaa atc gct aac tat ccg aac gaa aat caa aat aat agg gaa aat gta      96
Glu Ile Ala Asn Tyr Pro Asn Glu Asn Gln Asn Asn Arg Glu Asn Val
            20                  25                  30 agt gat gta ccc atg gat aca tcc tct atc agt aac gct gga atg atg     144
Ser Asp Val Pro Met Asp Thr Ser Ser Ile Ser Asn Ala Gly Met Met
        35                  40                  45 act gaa gaa ttt gaa att gac agt gta ttg gca cca cga tcg gct gaa     192
Thr Glu Glu Phe Glu Ile Asp Ser Val Leu Ala Pro Arg Ser Ala Glu
    50                  55                  60 acg gac gag gaa aaa ctg tat cgt gcg tgg gaa aat tgg gaa atg caa     240
Thr Asp Glu Glu Lys Leu Tyr Arg Ala Trp Glu Asn Trp Glu Met Gln
65                  70                  75                  80 agc gca gat gtt aga ttc ccc gca gtt gtt gga aca att ggg acc ctt     288
Ser Ala Asp Val Arg Phe Pro Ala Val Val Gly Thr Ile Gly Thr Leu
                85                  90                  95 tta gca aaa gaa atc gcg aaa tat gct ggg aaa aaa tta ctg aaa act     336
Leu Ala Lys Glu Ile Ala Lys Tyr Ala Gly Lys Lys Leu Leu Lys Thr
```

-continued

```
                   100                 105                 110
tta ttt gga tta cta ttt cca agt aat gat aca tta aca atg gaa gcg    384
Leu Phe Gly Leu Leu Phe Pro Ser Asn Asp Thr Leu Thr Met Glu Ala
        115                 120                 125 att ttg gaa gca act gag gaa atg atg aat cgt aaa ttg tca gaa gcg    432
Ile Leu Glu Ala Thr Glu Glu Met Met Asn Arg Lys Leu Ser Glu Ala
130                 135                 140 att aga gat aga gta act caa gaa ctg aaa ggg tta caa aat ggt ata    480
Ile Arg Asp Arg Val Thr Gln Glu Leu Lys Gly Leu Gln Asn Gly Ile
            145                 150                 155                 160 aca aat ttt tta gag gat gta gaa gat ttt gaa acg tat gct tct atg    528
Thr Asn Phe Leu Glu Asp Val Glu Asp Phe Glu Thr Tyr Ala Ser Met
                    165                 170                 175 tcc tta gaa cgc caa aaa tta tac aga ttt aaa aca aac aat cca aat    576
Ser Leu Glu Arg Gln Lys Leu Tyr Arg Phe Lys Thr Asn Asn Pro Asn
            180                 185                 190 ata gaa ccg aaa gct att ata gat agt att aac gag atg aat caa act    624
Ile Glu Pro Lys Ala Ile Ile Asp Ser Ile Asn Glu Met Asn Gln Thr
        195                 200                 205 ttc gat aac agg atg cct cag ttt aca tcg gat tat cca gaa tgg aag    672
Phe Asp Asn Arg Met Pro Gln Phe Thr Ser Asp Tyr Pro Glu Trp Lys
210                 215                 220 gta gag tta tta cct ttg ttt gca caa gcg gcg aat ctc cat ctt gtc    720
Val Glu Leu Leu Pro Leu Phe Ala Gln Ala Ala Asn Leu His Leu Val
225                 230                 235                 240 ttc tta aga gat gtc gtt aaa aat gca aca gat tgg gga cta acg gat    768
Phe Leu Arg Asp Val Val Lys Asn Ala Thr Asp Trp Gly Leu Thr Asp
                245                 250                 255 gca aac att gta cgc tat aca gac aga tta aaa gca cgt gta aag gaa    816
Ala Asn Ile Val Arg Tyr Thr Asp Arg Leu Lys Ala Arg Val Lys Glu
            260                 265                 270 tat tca aac tat gct tta cag aca tac aaa gag gca ttc gaa aac atg    864
Tyr Ser Asn Tyr Ala Leu Gln Thr Tyr Lys Glu Ala Phe Glu Asn Met
        275                 280                 285 tac tac agc aat ggg aag gtt att cca gca tta gat ttc cgt aat ttt    912
Tyr Tyr Ser Asn Gly Lys Val Ile Pro Ala Leu Asp Phe Arg Asn Phe
290                 295                 300 atg gtg ttt aat gta tta gat tat gtt tcc acg tgg tct atg tta cga    960
Met Val Phe Asn Val Leu Asp Tyr Val Ser Thr Trp Ser Met Leu Arg
305                 310                 315                 320 tat gaa gga att att atc aac tcg agt aca aac gta tat tcg tat ctc   1008
Tyr Glu Gly Ile Ile Ile Asn Ser Ser Thr Asn Val Tyr Ser Tyr Leu
                325                 330                 335 aag aat ctt gaa gta tcg gta cta cct tcc gcg cct agc tgg tcc gta   1056
Lys Asn Leu Glu Val Ser Val Leu Pro Ser Ala Pro Ser Trp Ser Val
            340                 345                 350 tta aat cag ttc ctt caa ggt aaa cca ttc aaa ata ttt tct ggg tta   1104
Leu Asn Gln Phe Leu Gln Gly Lys Pro Phe Lys Ile Phe Ser Gly Leu
        355                 360                 365 tcc tcg agg gca tac aaa caa ata gaa gat gga ttc cca tct cat ggt   1152
Ser Ser Arg Ala Tyr Lys Gln Ile Glu Asp Gly Phe Pro Ser His Gly
370                 375                 380 gtg act ttt aag aat tac aat gaa ata gat agt gta aga acg cat tat   1200
Val Thr Phe Lys Asn Tyr Asn Glu Ile Asp Ser Val Arg Thr His Tyr
385                 390                 395                 400 aaa gga ggc tct tac atc ggg cct ttt ggt agg caa gat aca cct cgt   1248
Lys Gly Gly Ser Tyr Ile Gly Pro Phe Gly Arg Gln Asp Thr Pro Arg
                405                 410                 415 tca ggg tcg gta tat tta gtt gaa ttc gaa aat tat aat aaa agc ttc   1296
```

|     |     |     |     |     |     |     |     |     |     |     |     |     |     |      |
|-----|-----|-----|-----|-----|-----|-----|-----|-----|-----|-----|-----|-----|-----|------|
| Ser | Gly | Ser | Val | Tyr | Leu | Val | Glu | Phe | Glu | Asn | Tyr | Asn | Lys | Ser Phe |
|     |     |     | 420 |     |     |     | 425 |     |     |     | 430 |     |     |      |

```
act ctt tct aat cca atc gac aat cca att acg agg att aaa caa caa    1344
Thr Leu Ser Asn Pro Ile Asp Asn Pro Ile Thr Arg Ile Lys Gln Gln
            435                 440                 445 aaa cat tac cag aaa gat caa ata cgg gaa gtg agt caa gat att ctt    1392
Lys His Tyr Gln Lys Asp Gln Ile Arg Glu Val Ser Gln Asp Ile Leu
    450                 455                 460 ata tat gag ccc ggg ggc agt tta aca aac aac tcg gga ggg tat tgg    1440
Ile Tyr Glu Pro Gly Gly Ser Leu Thr Asn Asn Ser Gly Gly Tyr Trp
465                 470                 475                 480 tct tct tat ccc gat tat aca gtc aaa cat gtg att gga tta cct tgg    1488
Ser Ser Tyr Pro Asp Tyr Thr Val Lys His Val Ile Gly Leu Pro Trp
                485                 490                 495 atg ggg gta cct act aca aat att cct tta tta act cat acc ggt agc    1536
Met Gly Val Pro Thr Thr Asn Ile Pro Leu Leu Thr His Thr Gly Ser
            500                 505                 510 ata gtc ctc cca cct cgt ttt cca gat acg tca gta gtt gca act ttt    1584
Ile Val Leu Pro Pro Arg Phe Pro Asp Thr Ser Val Val Ala Thr Phe
        515                 520                 525 agt cga aca caa att gcg cct tac acg cat ctg agt aat tat aca ttt    1632
Ser Arg Thr Gln Ile Ala Pro Tyr Thr His Leu Ser Asn Tyr Thr Phe
    530                 535                 540 aaa cat gca gtt ccg aac gat gga gca ggc ttc aca att tca cca tta    1680
Lys His Ala Val Pro Asn Asp Gly Ala Gly Phe Thr Ile Ser Pro Leu
545                 550                 555                 560 caa ttc acg aat tta tct ggt ttt aat gct gaa aaa gca tat ctt aga    1728
Gln Phe Thr Asn Leu Ser Gly Phe Asn Ala Glu Lys Ala Tyr Leu Arg
                565                 570                 575 gaa ctg ttc gga aat cat ggt gat gga gtt gta ttt cca gaa acg cga    1776
Glu Leu Phe Gly Asn His Gly Asp Gly Val Val Phe Pro Glu Thr Arg
            580                 585                 590 gat act agt gtg aca tac caa tat acc att tat aat cca act tca act    1824
Asp Thr Ser Val Thr Tyr Gln Tyr Thr Ile Tyr Asn Pro Thr Ser Thr
        595                 600                 605 act aga caa tac aga atc tat ctt aag ctc gcg act cca aat gga cca    1872
Thr Arg Gln Tyr Arg Ile Tyr Leu Lys Leu Ala Thr Pro Asn Gly Pro
    610                 615                 620 gca aag ttc tgg ctt cag ttt cat ggt gaa ggc agc gtt cga tat gat    1920
Ala Lys Phe Trp Leu Gln Phe His Gly Glu Gly Ser Val Arg Tyr Asp
625                 630                 635                 640 gta gat act cgt gac ctt aat gat ggt atc aat gat aat ggg gcg act    1968
Val Asp Thr Arg Asp Leu Asn Asp Gly Ile Asn Asp Asn Gly Ala Thr
                645                 650                 655 ttt cac gag aaa cat tat aac act ata act ata cca gcg ggt gaa cac    2016
Phe His Glu Lys His Tyr Asn Thr Ile Thr Ile Pro Ala Gly Glu His
            660                 665                 670 tat gtc cta ggt ctt gag cat caa gga cct gcg gct att tta gga agg    2064
Tyr Val Leu Gly Leu Glu His Gln Gly Pro Ala Ala Ile Leu Gly Arg
        675                 680                 685 att atg ttg act cct aca aat gta aca cca att tat                    2100
Ile Met Leu Thr Pro Thr Asn Val Thr Pro Ile Tyr
    690                 695                 700

<210> SEQ ID NO 2
<211> LENGTH: 700
<212> TYPE: PRT
<213> ORGANISM: Bacillus thuringiensis

<400> SEQUENCE: 2
```

```
Met Lys Asn Asn Gln Thr His Phe Ser Asp Glu Leu Thr Asn His Ile
 1               5                  10                  15

Glu Ile Ala Asn Tyr Pro Asn Glu Asn Gln Asn Asn Arg Glu Asn Val
             20                  25                  30

Ser Asp Val Pro Met Asp Thr Ser Ser Ile Ser Asn Ala Gly Met Met
         35                  40                  45

Thr Glu Glu Phe Glu Ile Asp Ser Val Leu Ala Pro Arg Ser Ala Glu
 50                  55                  60

Thr Asp Glu Glu Lys Leu Tyr Arg Ala Trp Glu Asn Trp Glu Met Gln
 65                  70                  75                  80

Ser Ala Asp Val Arg Phe Pro Ala Val Val Gly Thr Ile Gly Thr Leu
                 85                  90                  95

Leu Ala Lys Glu Ile Ala Lys Tyr Ala Gly Lys Lys Leu Leu Lys Thr
             100                 105                 110

Leu Phe Gly Leu Leu Phe Pro Ser Asn Asp Thr Leu Thr Met Glu Ala
         115                 120                 125

Ile Leu Glu Ala Thr Glu Met Met Asn Arg Lys Leu Ser Glu Ala
 130                 135                 140

Ile Arg Asp Arg Val Thr Gln Glu Leu Lys Gly Leu Gln Asn Gly Ile
145                 150                 155                 160

Thr Asn Phe Leu Glu Asp Val Glu Asp Phe Glu Thr Tyr Ala Ser Met
             165                 170                 175

Ser Leu Glu Arg Gln Lys Leu Tyr Arg Phe Lys Thr Asn Asn Pro Asn
         180                 185                 190

Ile Glu Pro Lys Ala Ile Ile Asp Ser Ile Asn Glu Met Asn Gln Thr
 195                 200                 205

Phe Asp Asn Arg Met Pro Gln Phe Thr Ser Asp Tyr Pro Glu Trp Lys
 210                 215                 220

Val Glu Leu Leu Pro Leu Phe Ala Gln Ala Ala Asn Leu His Leu Val
225                 230                 235                 240

Phe Leu Arg Asp Val Val Lys Asn Ala Thr Asp Trp Gly Leu Thr Asp
             245                 250                 255

Ala Asn Ile Val Arg Tyr Thr Asp Arg Leu Lys Ala Arg Val Lys Glu
         260                 265                 270

Tyr Ser Asn Tyr Ala Leu Gln Thr Tyr Lys Glu Ala Phe Glu Asn Met
 275                 280                 285

Tyr Tyr Ser Asn Gly Lys Val Ile Pro Ala Leu Asp Phe Arg Asn Phe
 290                 295                 300

Met Val Phe Asn Val Leu Asp Tyr Val Ser Thr Trp Ser Met Leu Arg
305                 310                 315                 320

Tyr Glu Gly Ile Ile Asn Ser Ser Thr Asn Val Tyr Ser Tyr Leu
             325                 330                 335

Lys Asn Leu Glu Val Ser Val Leu Pro Ser Ala Pro Ser Trp Ser Val
             340                 345                 350

Leu Asn Gln Phe Leu Gln Gly Lys Pro Phe Lys Ile Phe Ser Gly Leu
         355                 360                 365

Ser Ser Arg Ala Tyr Lys Gln Ile Glu Asp Gly Phe Pro Ser His Gly
 370                 375                 380

Val Thr Phe Lys Asn Tyr Asn Glu Ile Asp Ser Val Arg Thr His Tyr
385                 390                 395                 400

Lys Gly Gly Ser Tyr Ile Gly Pro Gly Arg Gln Asp Thr Pro Arg
             405                 410                 415

Ser Gly Ser Val Tyr Leu Val Glu Phe Glu Asn Tyr Asn Lys Ser Phe
```

-continued

```
            420                 425                 430

Thr Leu Ser Asn Pro Ile Asp Asn Pro Ile Thr Arg Ile Lys Gln Gln
        435                 440                 445

Lys His Tyr Gln Lys Asp Gln Ile Arg Glu Val Ser Gln Asp Ile Leu
    450                 455                 460

Ile Tyr Glu Pro Gly Gly Ser Leu Thr Asn Asn Ser Gly Gly Tyr Trp
465                 470                 475                 480

Ser Ser Tyr Pro Asp Tyr Thr Val Lys His Val Ile Gly Leu Pro Trp
                485                 490                 495

Met Gly Val Pro Thr Thr Asn Ile Pro Leu Leu Thr His Thr Gly Ser
            500                 505                 510

Ile Val Leu Pro Pro Arg Phe Pro Asp Thr Ser Val Val Ala Thr Phe
        515                 520                 525

Ser Arg Thr Gln Ile Ala Pro Tyr Thr His Leu Ser Asn Tyr Thr Phe
    530                 535                 540

Lys His Ala Val Pro Asn Asp Gly Ala Gly Phe Thr Ile Ser Pro Leu
545                 550                 555                 560

Gln Phe Thr Asn Leu Ser Gly Phe Asn Ala Glu Lys Ala Tyr Leu Arg
                565                 570                 575

Glu Leu Phe Gly Asn His Gly Asp Gly Val Val Phe Pro Glu Thr Arg
            580                 585                 590

Asp Thr Ser Val Thr Tyr Gln Tyr Thr Ile Tyr Asn Pro Thr Ser Thr
        595                 600                 605

Thr Arg Gln Tyr Arg Ile Tyr Leu Lys Leu Ala Thr Pro Asn Gly Pro
    610                 615                 620

Ala Lys Phe Trp Leu Gln Phe His Gly Glu Gly Ser Val Arg Tyr Asp
625                 630                 635                 640

Val Asp Thr Arg Asp Leu Asn Asp Gly Ile Asn Asp Asn Gly Ala Thr
                645                 650                 655

Phe His Glu Lys His Tyr Asn Thr Ile Thr Ile Pro Ala Gly Glu His
            660                 665                 670

Tyr Val Leu Gly Leu Glu His Gln Gly Pro Ala Ala Ile Leu Gly Arg
        675                 680                 685

Ile Met Leu Thr Pro Thr Asn Val Thr Pro Ile Tyr
    690                 695                 700

<210> SEQ ID NO 3
<211> LENGTH: 706
<212> TYPE: PRT
<213> ORGANISM: Paenibacillus popilliae

<400> SEQUENCE: 3

Met Asn Asn Asn Phe Asn Gly Gly Asn Asn Thr Gly Asn Asn Phe Thr
 1               5                  10                  15

Gly Asn Thr Leu Ser Asn Gly Ile Cys Thr Lys Lys Asn Met Lys Gly
            20                  25                  30

Thr Leu Ser Arg Thr Ala Ile Phe Ser Asp Gly Ile Ser Asp Asp Leu
        35                  40                  45

Ile Cys Cys Leu Asp Pro Ile Tyr Asn Asn Asn Asp Asn Asn Asn Asp
    50                  55                  60

Ala Ile Cys Asp Glu Leu Gly Leu Thr Pro Ile Asp Asn Asn Thr Ile
65                  70                  75                  80

Cys Ser Thr Asp Phe Thr Pro Ile Asn Val Met Arg Thr Asp Pro Phe
                85                  90                  95
```

-continued

```
Arg Lys Lys Ser Thr Gln Glu Leu Thr Arg Glu Trp Thr Glu Trp Lys
            100                 105                 110
Glu Asn Ser Pro Ser Leu Phe Thr Pro Ala Ile Val Gly Val Val Thr
        115                 120                 125
Ser Phe Leu Leu Gln Ser Leu Lys Lys Gln Ala Thr Ser Phe Leu Leu
    130                 135                 140
Lys Thr Leu Thr Asp Leu Leu Phe Pro Asn Asn Ser Ser Leu Thr Met
145                 150                 155                 160
Glu Glu Ile Leu Arg Ala Thr Glu Gln Tyr Val Gln Glu Arg Leu Asp
                165                 170                 175
Thr Asp Thr Ala Asn Arg Val Ser Gln Glu Leu Val Gly Leu Lys Asn
            180                 185                 190
Asn Leu Thr Thr Phe Asn Asp Gln Val Glu Asp Phe Leu Gln Asn Arg
        195                 200                 205
Val Gly Ile Ser Pro Leu Ala Ile Ile Asp Ser Ile Asn Thr Met Gln
    210                 215                 220
Gln Leu Phe Val Asn Arg Leu Pro Gln Phe Gln Val Ser Gly Tyr Gln
225                 230                 235                 240
Val Leu Leu Leu Pro Leu Phe Ala Gln Ala Ala Thr Leu His Leu Thr
                245                 250                 255
Phe Leu Arg Asp Val Ile Ile Asn Ala Asp Glu Trp Asn Ile Pro Thr
            260                 265                 270
Ala Gln Leu Asn Thr Tyr Thr Arg Tyr Phe Lys Glu Tyr Ile Ala Glu
        275                 280                 285
Tyr Ser Asn Tyr Ala Leu Ser Thr Tyr Asp Asp Gly Phe Arg Thr Arg
    290                 295                 300
Phe Tyr Pro Arg Asn Thr Leu Glu Asp Met Leu Gln Phe Lys Thr Phe
305                 310                 315                 320
Met Thr Leu Asn Ala Leu Asp Leu Val Ser Ile Trp Ser Leu Leu Lys
                325                 330                 335
Tyr Val Asn Leu Tyr Val Ser Thr Ser Ala Asn Leu Tyr Asn Ile Gly
            340                 345                 350
Asp Asn Lys Val Asn Glu Gly Ala Tyr Pro Ile Ser Tyr Gly Pro Phe
        355                 360                 365
Phe Asn Ser Tyr Ile Gln Thr Lys Ser Asn Tyr Val Leu Ser Gly Val
    370                 375                 380
Ser Gly Ile Gly Ala Arg Phe Thr Tyr Ser Thr Val Leu Gly Arg Tyr
385                 390                 395                 400
Leu His Asp Asp Leu Lys Asn Ile Ile Thr Thr Tyr Val Gly Gly Thr
                405                 410                 415
Gln Gly Pro Asn Ile Gly Val Gln Leu Ser Thr Glu Leu Asp Glu
            420                 425                 430
Leu Lys Lys Gln Gln Gln Ala Thr Arg Asp Ser Leu Val Asp Phe Gln
        435                 440                 445
Phe Phe Thr Leu Asn Cys Met Leu Pro Asn Pro Ile Thr Ala Pro Tyr
    450                 455                 460
Phe Ala Thr Ser Leu Tyr Glu Ser Arg Tyr Ser Ser Ile Gly Gly Tyr
465                 470                 475                 480
Leu Arg Lys Asp Val Phe Lys Ser Glu Asp Ser Thr Cys Gly Leu Gly
                485                 490                 495
Asn Pro Gly Ala Trp Thr Ser Tyr Pro Asp Tyr Tyr Ile Thr Asn Ile
            500                 505                 510
Ser Ala Thr Val Gln Ile Asn Gly Glu Asn Thr Asp Thr Thr Pro Leu
```

-continued

```
        515                 520                 525

Tyr Phe Lys Glu Asn Arg Pro Ile Thr Ser Thr Arg Gly Val Asn Lys
    530                 535                 540

Val Ile Ala Val Tyr Asn Arg Lys Ala Asn Ile Ala Gly Thr Asn Gln
545                 550                 555                 560

Asn Gly Thr Met Ile His Gln Ala Pro Pro Asp Gly Thr Gly Phe Thr
                565                 570                 575

Val Ser Pro Leu His Pro Ser Ala Asn Thr Ile Thr Ser Tyr Ile Lys
            580                 585                 590

Glu Asn Tyr Gly Asn Ser Gly Asp Ser Leu His Leu Lys Gly Gln Gly
        595                 600                 605

Tyr Leu His Tyr Met Leu Ser Gly Asn Gly Gln Asp Arg Tyr Arg Leu
    610                 615                 620

Val Leu Arg Leu Ser Gly Ala Ala Asn Gln Ile Lys Leu Gln Ser Pro
625                 630                 635                 640

Thr Thr Ser Ile Tyr Ala Phe Asp Thr Ser Thr Asn Asn Glu Gly Ile
                645                 650                 655

Thr Asp Asn Gly Ser Lys Phe Lys Asp Phe Ala Phe Ser Thr Pro Phe
            660                 665                 670

Val Ile Pro Glu Gln Lys Glu Ile Val Leu Tyr Phe Glu Gly Val Gly
        675                 680                 685

Ser Leu Asp Leu Met Asn Leu Ile Phe Leu Pro Ala Asp Asp Thr Pro
    690                 695                 700

Leu Tyr
705

<210> SEQ ID NO 4
<211> LENGTH: 675
<212> TYPE: PRT
<213> ORGANISM: Paenibacillus popilliae
<400> SEQUENCE: 4

Met Asn Asn Asn Gly Asn Ala Leu Ser Arg Thr Ala Leu Thr Pro Thr
 1               5                  10                  15

Asn Asn Lys Val Ile Ser Gly Asp Leu Val Thr Asn Gly Leu Pro Pro
            20                  25                  30

Ile Asp Asn Asn Ile Ile Cys Ser Asn Gly Phe Met Pro Ile Asn Val
        35                  40                  45

Thr Arg Lys Asn Pro Phe Arg Lys Arg Thr Thr Gln Glu Phe Ile Arg
    50                  55                  60

Glu Trp Thr Glu Trp Lys Glu Asn Ser Pro Ser Leu Phe Thr Ala Pro
65                  70                  75                  80

Ile Val Gly Val Val Thr Ser Thr Leu Leu Glu Ala Leu Lys Lys Gln
                85                  90                  95

Val Gln Ser Arg Leu Leu Leu Leu Met Thr Asn Leu Leu Phe Pro Asn
            100                 105                 110

Asn Ser Thr Ser Thr Met Glu Glu Ile Leu Arg Ala Thr Glu Gln Tyr
        115                 120                 125

Val Gln Glu Gln Leu Asp Thr Val Thr Trp Asn Arg Val Ser Gln Glu
    130                 135                 140

Leu Glu Gly Leu Lys Asn Asn Leu Arg Thr Phe Asn Asp Gln Ile Asp
145                 150                 155                 160

Asp Phe Leu Gln Asn Arg Val Glu Ile Ser Pro Thr Ala Met Ile Asp
                165                 170                 175
```

-continued

```
Ser Ile Asn Thr Met Gln Gln Val Phe Val Asn Arg Leu Pro Gln Phe
            180                 185                 190

Gln Leu Ser Asp Tyr Gln Leu Leu Leu Pro Leu Phe Ala Gln Gly
        195                 200                 205

Ala Thr Leu His Leu Thr Phe Ile Arg Asp Ile Ile Asn Ala Gly
        210                 215                 220

Glu Trp Asn Ile Pro Glu Ala Gln Leu Asn Thr Cys Lys Arg Tyr Leu
225                 230                 235                 240

Lys Gln Tyr Val Ala Gln Tyr Ser Asn Tyr Ala Leu Ser Thr Tyr Glu
                245                 250                 255

Gly Ala Phe Arg Ala Arg Phe Tyr Pro Arg Ala Thr Leu Glu Asn Met
            260                 265                 270

Leu Gln Phe Lys Thr Phe Met Thr Leu Asn Val Leu Asp Leu Val Ser
        275                 280                 285

Ile Trp Ser Leu Leu Lys Tyr Met Asn Leu Tyr Ile Ser Thr Ser Ala
    290                 295                 300

Asn Leu Tyr Asn Ile Gly Asp Asn Lys Val Asn Glu Gly Glu Tyr Ser
305                 310                 315                 320

Ile Ser Tyr Trp Pro Phe Phe Asn Ser Tyr Ile Gln Thr Lys Ser Asn
                325                 330                 335

Tyr Val Leu Ser Gly Val Ser Gly Tyr Ala Ile Arg Trp Tyr Tyr Leu
            340                 345                 350

Asn Thr Phe Phe Gly Glu Tyr Ile Gln Asp Asn Leu Tyr Asn Ile Ile
        355                 360                 365

Ala Ser Tyr Val Gly Gly Val Asn Gly Pro Lys Ile Gly Val Gln Leu
    370                 375                 380

Ser Thr Thr Glu Leu Asp Lys Gln Ile Lys Gln Gln Ala Arg Ala Gly
385                 390                 395                 400

Met Pro Thr Gly Leu Asp Asp Leu Ser Phe Asn Cys Thr Leu Arg Asn
                405                 410                 415

Pro Thr Thr Val Pro Tyr Phe Ala Cys Asn Phe Gln Glu Leu Thr Ser
            420                 425                 430

Ser Gly Thr Ala Gly Thr Gly Phe Ile Arg Ser Asp Val Phe Arg
        435                 440                 445

Ser Glu Asp Asn Ile Cys Gly Leu Gly Thr Gly Tyr Ala Ser Ala Trp
    450                 455                 460

Thr Ser Tyr Pro Asp Tyr Tyr Ile Thr Asn Ile Ser Ala Thr Val Gln
465                 470                 475                 480

Val Asp Gly Ile Asn Ile Asp Ile Thr Pro Leu Cys Phe Gly Glu Asp
                485                 490                 495

Arg Ala Ile Thr Ser Thr His Gly Val Asn Lys Val Ile Ala Val Tyr
            500                 505                 510

Asn Arg Lys Ala Asn Ile Ala Gly Thr Asn Gln Asn Gly Thr Met Ile
        515                 520                 525

His Gln Ala Pro Asn Asp Gly Thr Gly Phe Thr Val Ser Pro Leu His
    530                 535                 540

Leu Ala Ser Phe Thr His Pro Ser Glu Ala His Ile Gln Glu Asn Tyr
545                 550                 555                 560

Gly Asn Ser Gly Asp Ser Leu Arg Leu Thr Gly Pro Thr Thr Ala Ile
                565                 570                 575

Thr Tyr Met Leu Ser Gly Asp Gly Arg Thr Ile Tyr Lys Leu Val Leu
            580                 585                 590

Arg Val Ser Gly Val Ile Thr Arg Ile Thr Ala Lys Val Arg Gly Asn
```

```
                595             600             605
Ser Ile Gly Tyr Leu Glu Tyr Ile Asn Thr Val Asp Asn Asn Gln Gly
    610                 615                 620

Ile Thr Asp Asn Gly Ser Lys Phe Gln Asp Phe Glu Phe Arg Pro Thr
625                 630                 635                 640

Ile Thr Ile Asp Ala Gln Thr Pro Ile Val Leu Glu Phe Ser Ala Thr
                645                 650                 655

Ser Asn Phe Asp Leu Met Asn Leu Ile Phe Ile Pro Tyr Tyr Asp Thr
                660                 665                 670

Pro Ile Tyr
        675

<210> SEQ ID NO 5
<211> LENGTH: 695
<212> TYPE: PRT
<213> ORGANISM: Paenibacillus popilliae

<400> SEQUENCE: 5

Met Asn Asn Tyr Phe Ile Gly Lys Val Leu Ser Gly His His Ile Asn
 1               5                  10                  15

Asn Asn Gly Asn Gly Asn Thr Leu Ser Arg Thr Ala Leu Thr Pro Thr
            20                  25                  30

Asn Asn Asn Val Asn Arg Gly Asp Leu Val Thr Asn Gly Leu Thr Pro
        35                  40                  45

Ile Asp Asn As

```
Leu Glu Phe Lys Thr Phe Met Thr Leu Asn Val Leu Asp Leu Val Ser
    290                 295                 300

Met Trp Ser Leu Leu Lys Tyr Val Asn Leu Tyr Val Ser Thr Ser Ala
305                 310                 315                 320

Asn Leu Tyr Asn Ile Gly Asp Asn Lys Val Asn Glu Gly Glu Tyr Ser
                325                 330                 335

Ile Ser Tyr Trp Pro Phe Phe Asn Thr Tyr Ile Gln Thr Lys Ser Asn
                340                 345                 350

Tyr Val Leu Ser Gly Val Ser Gly Tyr Ala Met Arg Trp Ser Tyr Thr
                355                 360                 365

Asn Pro Phe Phe Gly Glu Tyr Ile Gln Asp His Leu Tyr Asn Ile Thr
370                 375                 380

Ala Ser Tyr Ile Gly Gly Val Asn Gly Pro Gln Ile Gly Gln Gln Leu
385                 390                 395                 400

Ser Thr Thr Glu Leu Asp Gln Leu Val Gln Gln Ala Arg Ala Asp
                405                 410                 415

Ile Pro Val Asp Phe Thr Gln Ile Pro Ile Asn Cys Thr Leu Arg Asn
                420                 425                 430

Pro Leu Glu Val Pro Tyr Tyr Ala Thr Arg Phe Asn Glu Leu Thr Ser
                435                 440                 445

Leu Gly Thr Ala Gly Val Gly Gly Phe Val Arg Ser Asp Val Phe Ile
450                 455                 460

Ser Asn Asp Ser Val Cys Gly Leu Gly Thr Asn Tyr Ser Ser Gly Gln
465                 470                 475                 480

Thr Phe Tyr Pro Asp Tyr Tyr Ile Thr Asn Ile Ser Ala Thr Val Gln
                485                 490                 495

Val Asn Gly Thr Asn Thr Asp Ile Ser Pro Leu Tyr Phe Gly Glu Asn
                500                 505                 510

Arg Ala Ile Thr Ser Thr Asn Gly Val Asn Lys Val Ile Ala Ile Tyr
                515                 520                 525

Asn Arg Lys Thr Asn Tyr Asp Asp Phe Thr Asn Ile Arg Gly Thr Ile
                530                 535                 540

Val His Glu Ala Pro Thr Asp Ser Thr Gly Phe Thr Ile Ser Pro Leu
545                 550                 555                 560

His Leu Asp Thr Val Asn Ile Asn Ser Tyr Leu Tyr Ile Gln Glu Asn
                565                 570                 575

Tyr Gly Asn Asn Gly Asp Ser Leu Arg Val Ile Asn Arg Ala Ile Ile
                580                 585                 590

Lys Tyr Arg Leu Ser Ala Ala Arg Ser Val Ile Tyr Arg Leu Val Leu
                595                 600                 605

Arg Val Ser Gly Thr Ala Ser Ser Ile Val Ala Ile Tyr Glu Asn Tyr
610                 615                 620

Pro Val Gly Ser Ala Asn Gln Ile Asn Thr Gly Thr Asp Asn Glu Gly
625                 630                 635                 640

Val Ile Asp Asn Asp Ser Lys Phe Ile Asp Leu Ile Phe Asn Thr Pro
                645                 650                 655

Phe Ser Val Ser Gly Thr Ala Arg Glu Leu Gln Leu Gln Val Ser Gly
                660                 665                 670

Ala Thr Thr Ser Ser Pro Leu Asp Ile Met Asn Ile Ile Leu Ile Pro
                675                 680                 685

Ile Asn Asp Val Pro Leu Tyr
690                 695
```

<210> SEQ ID NO 6
<211> LENGTH: 633
<212> TYPE: PRT
<213> ORGANISM: Bacillus thuringiensis

<400> SEQUENCE: 6

```
Met Asn Asn Val Leu Asn Ser Gly Arg Thr Thr Ile Cys Asp Ala Tyr
  1               5                  10                  15

Asn Val Val Ala His Asp Pro Phe Ser Phe Glu His Lys Ser Leu Asp
             20                  25                  30

Thr Ile Gln Lys Glu Trp Met Glu Trp Lys Arg Thr Asp His Ser Leu
         35                  40                  45

Tyr Val Ala Pro Val Val Gly Thr Val Ser Ser Phe Leu Leu Lys Lys
     50                  55                  60

Val Gly Ser Leu Ile Gly Lys Arg Ile Leu Glu Leu Trp Gly Ile
 65                  70                  75                  80

Ile Phe Pro Ser Gly Ser Thr Asn Leu Met Gln Asp Ile Leu Arg Glu
                 85                  90                  95

Thr Glu Gln Phe Leu Asn Gln Arg Leu Asn Thr Asp Thr Leu Ala Arg
            100                 105                 110

Val Asn Ala Glu Leu Ile Gly Leu Gln Ala Asn Ile Arg Glu Phe Asn
        115                 120                 125

Gln Gln Val Asp Asn Phe Leu Asn Pro Thr Gln Asn Pro Val Pro Leu
    130                 135                 140

Ser Ile Thr Ser Ser Val Asn Thr Met Gln Gln Leu Phe Leu Asn Arg
145                 150                 155                 160

Leu Pro Gln Phe Gln Ile Gln Gly Tyr Gln Leu Leu Leu Pro Leu
                165                 170                 175

Phe Ala Gln Ala Ala Asn Met His Leu Ser Phe Ile Arg Asp Val Ile
            180                 185                 190

Leu Asn Ala Asp Glu Trp Gly Ile Ser Ala Ala Thr Leu Arg Thr Tyr
        195                 200                 205

Arg Asp Tyr Leu Arg Asn Tyr Thr Arg Asp Tyr Ser Asn Tyr Cys Ile
    210                 215                 220

Asn Thr Tyr Gln Thr Ala Phe Arg Gly Leu Asn Thr Arg Leu His Asp
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Met Val Ser Ser Gly
            260                 265                 270

Ala Asn Leu Tyr Ala Ser Gly Ser Gly Pro Gln Gln Thr Gln Ser Phe
        275                 280                 285

Thr Ala Gln Asn Trp Pro Phe Leu Tyr Ser Leu Phe Gln Val Asn Ser
    290                 295                 300

Asn Tyr Ile Leu Ser Gly Ile Ser Gly Thr Arg Leu Ser Ile Thr Phe
305                 310                 315                 320

Pro Asn Ile Gly Gly Leu Pro Gly Ser Thr Thr Thr His Ser Leu Asn
                325                 330                 335

Ser Ala Arg Val Asn Tyr Ser Gly Gly Val Ser Ser Gly Leu Ile Gly
            340                 345                 350

Ala Thr Asn Leu Asn His Asn Phe Asn Cys Ser Thr Val Leu Pro Pro
        355                 360                 365

Leu Ser Thr Pro Phe Val Arg Ser Trp Leu Asp Ser Gly Thr Asp Arg
    370                 375                 380
```

-continued

```
Glu Gly Val Ala Thr Ser Thr Asn Trp Gln Thr Glu Ser Phe Gln Thr
385                 390                 395                 400

Thr Leu Ser Leu Arg Cys Gly Ala Phe Ser Ala Arg Gly Asn Ser Asn
                405                 410                 415

Tyr Phe Pro Asp Tyr Phe Ile Arg Asn Ile Ser Gly Val Pro Leu Val
            420                 425                 430

Ile Arg Asn Glu Asp Leu Thr Arg Pro Leu His Tyr Asn Gln Ile Arg
        435                 440                 445

Asn Ile Glu Ser Pro Ser Gly Thr Pro Gly Gly Ala Arg Ala Tyr Leu
    450                 455                 460

Val Ser Val His Asn Arg Lys Asn Asn Ile Tyr Ala Ala Asn Glu Asn
465                 470                 475                 480

Gly Thr Met Ile His Leu Ala Pro Glu Asp Tyr Thr Gly Phe Thr Ile
                485                 490                 495

Ser Pro Ile His Ala Thr Gln Val Asn Asn Gln Thr Arg Thr Phe Ile
            500                 505                 510

Ser Glu Lys Phe Gly Asn Gln Gly Asp Ser Leu Arg Phe Glu Gln Ser
        515                 520                 525

Asn Thr Thr Ala Arg Tyr Thr Leu Arg Gly Asn Gly Asn Ser Tyr Asn
    530                 535                 540

Leu Tyr Leu Arg Val Ser Ser Ile Gly Asn Ser Thr Ile Arg Val Thr
545                 550                 555                 560

Ile Asn Gly Arg Val Tyr Thr Val Ser Asn Val Asn Thr Thr Thr Asn
                565                 570                 575

Asn Asp Gly Val Asn Asp Asn Gly Ala Arg Phe Ser Asp Ile Asn Ile
            580                 585                 590

Gly Asn Ile Val Ala Ser Asp Asn Thr Asn Val Thr Leu Asp Ile Asn
        595                 600                 605

Val Thr Leu Asn Ser Gly Thr Pro Phe Asp Leu Met Asn Ile Met Phe
    610                 615                 620

Val Pro Thr Asn Leu Pro Pro Leu Tyr
625                 630

<210> SEQ ID NO 7
<211> LENGTH: 633
<212> TYPE: PRT
<213> ORGANISM: Bacillus thuringiensis

<400> SEQUENCE: 7

Met Asn Ser Val Leu Asn Ser Gly Arg Thr Thr Ile Cys Asp Ala Tyr
1               5                   10                  15

Asn Val Ala Ala His Asp Pro Phe Ser Phe Gln His Lys Ser Leu Asp
            20                  25                  30

Thr Val Gln Lys Glu Trp Thr Glu Trp Lys Asn Asn His Ser Leu
        35                  40                  45

Tyr Leu Asp Pro Ile Val Gly Thr Val Ala Ser Phe Leu Leu Lys Lys
    50                  55                  60

Val Gly Ser Leu Val Gly Lys Arg Ile Leu Ser Glu Leu Arg Asn Leu
65                  70                  75                  80

Ile Phe Pro Ser Gly Ser Thr Asn Leu Met Gln Asp Ile Leu Arg Glu
                85                  90                  95

Thr Glu Lys Phe Leu Asn Gln Arg Leu Asn Thr Asp Thr Leu Ala Arg
            100                 105                 110

Val Asn Ala Glu Leu Thr Gly Leu Gln Ala Asn Val Glu Glu Phe Asn
        115                 120                 125
```

-continued

```
Arg Gln Val Asp Asn Phe Leu Asn Pro Asn Arg Asn Ala Val Pro Leu
    130                 135                 140

Ser Ile Thr Ser Ser Val Asn Thr Met Gln Gln Leu Phe Leu Asn Arg
145                 150                 155                 160

Leu Pro Gln Phe Gln Met Gln Gly Tyr Gln Leu Leu Leu Pro Leu
                165                 170                 175

Phe Ala Gln Ala Ala Asn Leu His Leu Ser Phe Ile Arg Asp Val Ile
                180                 185                 190

Leu Asn Ala Asp Glu Trp Gly Ile Ser Ala Ala Thr Leu Arg Thr Tyr
            195                 200                 205

Arg Asp Tyr Leu Lys Asn Tyr Thr Arg Asp Tyr Ser Asn Tyr Cys Ile
    210                 215                 220

Asn Thr Tyr Gln Ser Ala Phe Lys Gly Leu Asn Thr Arg Leu His Asp
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Leu Val Ser Ser Gly
            260                 265                 270

Ala Asn Leu Tyr Ala Ser Gly Ser Gly Pro Gln Gln Thr Gln Ser Phe
    275                 280                 285

Thr Ser Gln Asp Trp Pro Phe Leu Tyr Ser Leu Phe Gln Val Asn Ser
    290                 295                 300

Asn Tyr Val Leu Asn Gly Phe Ser Gly Ala Arg Leu Ser Asn Thr Phe
305                 310                 315                 320

Pro Asn Ile Val Gly Leu Pro Gly Ser Thr Thr Thr His Ala Leu Leu
                325                 330                 335

Ala Ala Arg Val Asn Tyr Ser Gly Gly Ile Ser Ser Gly Asp Ile Gly
            340                 345                 350

Ala Ser Pro Phe Asn Gln Asn Phe Asn Cys Ser Thr Phe Leu Pro Pro
    355                 360                 365

Leu Leu Thr Pro Phe Val Arg Ser Trp Leu Asp Ser Gly Ser Asp Arg
    370                 375                 380

Glu Gly Val Ala Thr Val Thr Asn Trp Gln Thr Glu Ser Phe Glu Thr
385                 390                 395                 400

Thr Leu Gly Leu Arg Ser Gly Ala Phe Thr Ala Arg Gly Asn Ser Asn
                405                 410                 415

Tyr Phe Pro Asp Tyr Phe Ile Arg Asn Ile Ser Gly Val Pro Leu Val
                420                 425                 430

Val Arg Asn Glu Asp Leu Arg Arg Pro Leu His Tyr Asn Glu Ile Arg
    435                 440                 445

Asn Ile Ala Ser Pro Ser Gly Thr Pro Gly Gly Ala Arg Ala Tyr Met
    450                 455                 460

Val Ser Val His Asn Arg Lys Asn Asn Ile His Ala Val His Glu Asn
465                 470                 475                 480

Gly Ser Met Ile His Leu Ala Pro Asn Asp Tyr Thr Gly Phe Thr Ile
                485                 490                 495

Ser Pro Ile His Ala Thr Gln Val Asn Asn Gln Thr Arg Thr Phe Ile
                500                 505                 510

Ser Glu Lys Phe Gly Asn Gln Gly Asp Ser Leu Arg Phe Glu Gln Asn
            515                 520                 525

Asn Thr Thr Ala Arg Tyr Thr Leu Arg Gly Asn Gly Asn Ser Tyr Asn
530                 535                 540
```

```
Leu Tyr Leu Arg Val Ser Ser Ile Gly Asn Ser Thr Ile Arg Val Thr
545                 550                 555                 560

Ile Asn Gly Arg Val Tyr Thr Ala Thr Asn Val Asn Thr Thr Thr Asn
                565                 570                 575

Asn Asp Gly Val Asn Asp Asn Gly Ala Arg Phe Ser Asp Ile Asn Ile
            580                 585                 590

Gly Asn Val Val Ala Ser Ser Asn Ser Asp Val Pro Leu Asp Ile Asn
        595                 600                 605

Val Thr Leu Asn Ser Gly Thr Gln Phe Asp Leu Met Asn Ile Met Leu
    610                 615                 620

Val Pro Thr Asn Ile Ser Pro Leu Tyr
625                 630

<210> SEQ ID NO 8
<211> LENGTH: 622
<212> TYPE: PRT
<213> ORGANISM: Bacillus thuringiensis

<400> SEQUENCE: 8

Met Asn Thr Val Leu Asn Asn Gly Arg Asn Thr Thr Cys His Ala His
  1               5                  10                  15

Asn Val Val Ala His Asp Pro Phe Ser Phe Glu His Lys Ser Leu Asn
             20                  25                  30

Thr Ile Glu Lys Glu Trp Lys Glu Trp Lys Arg Thr Asp His Ser Leu
         35                  40                  45

Tyr Val Ala Pro Ile Val Gly Thr Val Gly Ser Phe Leu Leu Lys Lys
     50                  55                  60

Val Gly Ser Leu Val Gly Lys Arg Ile Leu Ser Glu Leu Gln Asn Leu
 65                  70                  75                  80

Ile Phe Pro Ser Gly Ser Ile Asp Leu Met Gln Glu Ile Leu Arg Ala
                 85                  90                  95

Thr Glu Gln Phe Ile Asn Gln Arg Leu Asn Ala Asp Thr Leu Gly Arg
            100                 105                 110

Val Asn Ala Glu Leu Ala Gly Leu Gln Ala Asn Val Ala Glu Phe Asn
        115                 120                 125

Arg Gln Val Asp Asn Phe Leu Asn Pro Asn Gln Asn Pro Val Pro Leu
    130                 135                 140

Ala Ile Ile Asp Ser Val Asn Thr Leu Gln Gln Leu Phe Leu Ser Arg
145                 150                 155                 160

Leu Pro Gln Phe Gln Ile Gln Gly Tyr Gln Leu Leu Leu Leu Pro Leu
                165                 170                 175

Phe Ala Gln Ala Ala Asn Phe Asn Leu Ser Phe Ile Arg Gly Val Ile
            180                 185                 190

Leu Asn Ala Asp Glu Trp Gly Ile Ser Ala Ala Thr Val Arg Thr Tyr
        195                 200                 205

Arg Asp His Leu Arg Lys Phe His Arg Asp Tyr Ser Asn Tyr Cys Ile
    210                 215                 220

Asn Pro Tyr Gln Thr Ala Phe Arg Gly Leu Asn His Arg Leu Pro Asp
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Leu Val Ser Ser Gly
            260                 265                 270

Ala Asn Leu Tyr Ala Ser Gly Ser Gly Pro Thr Gln Ser Phe Thr Ala
        275                 280                 285
```

```
Gln Asn Trp Pro Phe Leu Tyr Ser Leu Phe Gln Val Asn Ser Asn Tyr
    290                 295                 300

Val Leu Asn Gly Leu Ser Gly Ala Arg Thr Thr Ile Thr Phe Pro Asn
305                 310                 315                 320

Ile Gly Gly Leu Pro Val Tyr His Asn Ser Thr Leu His Phe Ala Arg
                325                 330                 335

Ile Asn Tyr Arg Gly Gly Val Ser Ser Arg Ile Gly Gln Ala Asn
        340                 345                 350

Leu Asn Gln Asn Phe Asn Ile Ser Thr Leu Phe Asn Pro Leu Gln Thr
            355                 360                 365

Pro Phe Ile Arg Ser Trp Leu Asp Ser Gly Thr Asp Arg Glu Gly Val
    370                 375                 380

Ala Thr Ser Thr Asn Trp Gln Ser Gly Ala Phe Glu Thr Thr Leu Leu
385                 390                 395                 400

Arg Phe Ser Ile Phe Ser Ala Arg Gly Asn Ser Asn Phe Phe Pro Asp
                405                 410                 415

Tyr Phe Ile Arg Asn Ile Ser Gly Val Val Gly Thr Ile Ser Asn Ala
                420                 425                 430

Asp Leu Ala Arg Pro Leu His Phe Asn Glu Ile Arg Asp Ile Gly Thr
            435                 440                 445

Thr Ala Val Ala Ser Leu Val Thr Val His Asn Arg Lys Asn Asn Ile
    450                 455                 460

Tyr Asp Thr His Glu Asn Gly Thr Met Ile His Leu Ala Pro Asn Asp
465                 470                 475                 480

Tyr Thr Gly Phe Thr Val Ser Pro Ile His Ala Thr Gln Val Asn Asn
                485                 490                 495

Gln Ile Arg Thr Phe Ile Ser Glu Lys Tyr Gly Asn Gln Gly Asp Ser
                500                 505                 510

Leu Arg Phe Glu Leu Ser Asn Pro Thr Ala Arg Tyr Thr Leu Arg Gly
            515                 520                 525

Asn Gly Asn Ser Tyr Asn Leu Tyr Leu Arg Val Ser Ser Ile Gly Ser
    530                 535                 540

Ser Thr Ile Arg Val Thr Ile Asn Gly Arg Val Tyr Thr Ala Asn Val
545                 550                 555                 560

Asn Thr Thr Thr Asn Asn Asp Gly Val Leu Asp Asn Gly Ala Arg Phe
                565                 570                 575

Ser Asp Ile Asn Ile Gly Asn Val Val Ala Ser Ala Asn Thr Asn Val
            580                 585                 590

Pro Leu Asp Ile Gln Val Thr Phe Asn Gly Asn Pro Gln Phe Glu Leu
    595                 600                 605

Met Asn Ile Met Phe Val Pro Thr Asn Leu Pro Pro Leu Tyr
    610                 615                 620

<210> SEQ ID NO 9
<211> LENGTH: 1163
<212> TYPE: PRT
<213> ORGANISM: Bacillus thuringiensis serovar finitimus

<400> SEQUENCE: 9

Met Asn Ser Glu Glu Met Asn His Val Asn Pro Phe Glu Ile Ser Asp
1               5                   10                  15

Asn Asn Asp Val Ser Ile Pro Ser Gln Arg Tyr Pro Phe Ala Asn Asp
            20                  25                  30

Pro Ala Asp Ser Val Phe Cys Ala Asp Asp Phe Leu Gln Ser Tyr Gly
```

-continued

```
               35                  40                  45
Glu Phe Asn Met Asp Asn Phe Gly Glu Ser Glu Pro Phe Ile Asp Ala
 50                  55                  60

Ser Gly Ala Ile Asn Ala Ala Ile Gly Val Thr Gly Thr Val Leu Gly
65                  70                  75                  80

Phe Leu Gly Val Pro Phe Ala Gly Ala Leu Thr Thr Phe Tyr Gln Lys
                 85                  90                  95

Leu Phe Gly Phe Leu Phe Pro Asn Asn Asn Thr Lys Gln Trp Glu Glu
                100                 105                 110

Phe Met Lys Gln Val Glu Ala Leu Ile Asp Glu Lys Ile Ser Asp Ala
                115                 120                 125

Val Arg Asn Lys Ala Ile Ser Glu Leu Gln Gly Leu Val Asn Asn Ile
130                 135                 140

Thr Leu Tyr Thr Glu Ala Leu Glu Glu Trp Leu Glu Asn Lys Glu Asn
145                 150                 155                 160

Pro Ala Val Arg Asp Arg Val Leu Gln Arg Trp Arg Ile Leu Asp Gly
                165                 170                 175

Phe Phe Glu Gln Gln Met Pro Ser Phe Ala Val Lys Gly Phe Glu Val
                180                 185                 190

Leu Leu Leu Val Val Tyr Thr Gln Ala Ala Asn Leu His Leu Leu Ser
                195                 200                 205

Leu Arg Asp Ala Tyr Ile Tyr Gly Ala Glu Trp Gly Leu Thr Pro Thr
210                 215                 220

Asn Ile Asp Gln Asn His Thr Arg Leu Leu Arg His Ser Ala Glu Tyr
225                 230                 235                 240

Thr Asp His Cys Val Asn Trp Tyr Asn Thr Gly Leu Lys Gln Leu Glu
                245                 250                 255

Asn Ser Asp Ala Lys Ser Trp Phe Gln Tyr Asn Arg Phe Arg Arg Glu
                260                 265                 270

Met Thr Leu Ser Val Leu Asp Val Ile Ala Leu Phe Pro Ala Tyr Asp
                275                 280                 285

Val Lys Met Tyr Pro Ile Pro Thr Asn Phe Gln Leu Thr Arg Glu Val
                290                 295                 300

Tyr Thr Asp Val Ile Gly Lys Ile Gly Arg Asn Asp Ser Asp His Trp
305                 310                 315                 320

Tyr Ser Ala Asn Ala Pro Ser Phe Ser Asn Leu Glu Ser Thr Leu Ile
                325                 330                 335

Arg Thr Pro His Val Val Asp Tyr Ile Lys Lys Leu Lys Ile Phe Tyr
                340                 345                 350

Ala Thr Val Asp Tyr Tyr Gly Ile Tyr Gly Arg Ser Gly Lys Trp Val
                355                 360                 365

Gly His Ile Ile Thr Ser Ala Thr Ser Ala Asn Thr Thr Glu Thr Arg
                370                 375                 380

Asn Tyr Gly Thr Ile Val Asn His Asp Ser Val Glu Leu Asn Phe Glu
385                 390                 395                 400

Gly Lys Asn Ile Tyr Lys Thr Gly Ser Leu Pro Gln Gly Val Pro Pro
                405                 410                 415

Tyr Gln Ile Gly Tyr Val Thr Pro Ile Tyr Phe Ile Thr Arg Ala Val
                420                 425                 430

Asn Phe Phe Thr Val Ser Gly Ser Lys Thr Ser Val Glu Lys Tyr Tyr
                435                 440                 445

Ser Lys Lys Asp Arg Tyr Tyr Ser Glu Gly Leu Pro Glu Glu Gln Gly
450                 455                 460
```

-continued

```
Val Phe Ser Thr Glu Gln Leu Pro Pro Asn Ser Ile Ala Glu Pro Glu
465                 470                 475                 480

His Ile Ala Tyr Ser His Arg Leu Cys His Val Thr Phe Ile Ser Val
                485                 490                 495

Ser Asn Gly Asn Lys Tyr Ser Lys Asp Leu Pro Leu Phe Ser Trp Thr
            500                 505                 510

His Ser Ser Val Asp Phe Asp Asn Tyr Val Tyr Pro Thr Lys Ile Thr
            515                 520                 525

Gln Leu Pro Ala Thr Lys Gly Tyr Asn Val Ser Ile Val Lys Glu Pro
        530                 535                 540

Gly Phe Ile Gly Gly Asp Ile Gly Lys Asn Asn Gly Gln Ile Leu Gly
545                 550                 555                 560

Lys Tyr Lys Val Asn Val Glu Asp Val Ser Gln Lys Tyr Arg Phe Arg
                565                 570                 575

Val Arg Tyr Ala Thr Glu Thr Glu Gly Glu Leu Gly Ile Lys Ile Asp
                580                 585                 590

Gly Arg Thr Val Asn Leu Tyr Gln Tyr Lys Lys Thr Lys Ala Pro Gly
            595                 600                 605

Asp Pro Leu Thr Tyr Lys Ala Phe Asp Tyr Leu Ser Phe Ser Thr Pro
        610                 615                 620

Val Lys Phe Asn Asn Ala Ser Ser Thr Ile Glu Leu Phe Leu Gln Asn
625                 630                 635                 640

Lys Thr Ser Gly Thr Phe Tyr Leu Ala Gly Ile Glu Ile Ile Pro Val
                645                 650                 655

Lys Ser Asn Tyr Glu Glu Leu Thr Leu Glu Glu Ala Lys Lys Ala
            660                 665                 670

Val Ser Ser Leu Phe Thr Asp Ala Arg Asn Ala Leu Lys Ile Asp Val
        675                 680                 685

Thr Asp Tyr Gln Ile Asp Gln Ala Ala Asn Leu Val Glu Cys Ile Ser
        690                 695                 700

Gly Asp Leu Tyr Ala Lys Glu Lys Ile Val Leu Leu Arg Ala Val Lys
705                 710                 715                 720

Phe Ala Lys Gln Leu Ser Gln Ser Gln Asn Leu Leu Ser Asp Pro Glu
                725                 730                 735

Phe Asn Asn Val Asn Arg Glu Asn Ser Trp Thr Ala Ser Thr Ser Val
            740                 745                 750

Ala Ile Ile Glu Gly Asp Pro Leu Tyr Lys Gly Arg Ala Val Gln Leu
        755                 760                 765

Ser Ser Ala Arg Asp Glu Asn Phe Pro Thr Tyr Leu Tyr Gln Lys Ile
770                 775                 780

Asp Glu Ser Thr Leu Lys Pro Tyr Thr Arg Tyr Gln Leu Arg Gly Phe
785                 790                 795                 800

Val Glu Gly Ser Glu Asn Leu Asp Val Tyr Leu Ile Arg Tyr Gly Ala
            805                 810                 815

Ala His Val Arg Met Asn Val Pro Tyr Asn Leu Glu Ile Ile Asp Thr
        820                 825                 830

Ser Ser Pro Val Asn Pro Cys Glu Glu Val Asp Gly Leu Ser His Arg
        835                 840                 845

Ser Cys Asn Val Phe Asp Arg Cys Lys Gln Ser Ile Ser Val Ala Pro
        850                 855                 860

Asp Ala Asn Thr Gly Pro Asp Gln Ile Asp Gly Asp Pro His Ala Phe
865                 870                 875                 880
```

```
Ser Phe His Ile Asp Thr Gly Thr Val Asp Ser Thr Glu Asn Leu Gly
            885                 890                 895
Ile Trp Val Ala Phe Lys Ile Ser Glu Leu Asp Gly Ser Ala Ile Phe
        900                 905                 910
Gly Asn Leu Glu Leu Ile Glu Val Gly Pro Leu Ser Gly Glu Ala Leu
            915                 920                 925
Ala Gln Val Gln Arg Lys Glu Lys Trp Lys Gln Val Leu Ala Lys
        930                 935                 940
Lys Arg Glu Thr Thr Ala Gln Thr Val Cys Ser Gly Glu Ala Ser Gln
945                 950                 955                 960
Leu Thr Asn Ser Ser Gln Ile Leu Lys Ile Arg Asn Tyr Asp Leu Ile
            965                 970                 975
Gln Asn Phe Arg Ile Phe Ser Leu Arg Asn Thr Leu Ser Ile Lys Phe
        980                 985                 990
Lys Ile Tyr Thr Ile Thr Asn Tyr Pro Tyr Ser Arg Leu Asn Tyr Asp
            995                 1000                1005
Leu Phe Met Glu Leu Glu Asn Arg Ile Gln Asn Ala Ser Leu Tyr Met
        1010                1015                1020
Thr Ser Asn Ile Leu Gln Asn Gly Gly Phe Lys Ser Asp Val Thr Ser
1025                1030                1035                1040
Trp Glu Thr Thr Ala Asn Ala Glu Val Gln Gln Ile Asp Gly Ala Ser
            1045                1050                1055
Val Leu Val Leu Ser Asn Trp Asn Ala Ser Val Ala Gln Ser Val Asn
        1060                1065                1070
Val Gln Asn Asp His Gly Tyr Val Leu Arg Val Thr Ala Lys Lys Glu
        1075                1080                1085
Gly Ile Gly Asn Gly Tyr Val Thr Ile Leu Asp Cys Ala Asn His Ile
        1090                1095                1100
Asp Thr Leu Thr Phe Ser Ala Cys Arg Ser Asp Ser Asp Thr Ser Ser
1105                1110                1115                1120
Asn Glu Leu Thr Ala Tyr Val Thr Lys Thr Leu Glu Ile Phe Pro Asp
            1125                1130                1135
Thr Glu Gln Ile Arg Ile Glu Ile Gly Glu Thr Glu Gly Met Phe Tyr
        1140                1145                1150
Val Glu Ser Val Glu Leu Ile Arg Met Glu Asn
        1155                1160

<210> SEQ ID NO 10
<211> LENGTH: 2055
<212> TYPE: DNA
<213> ORGANISM: Bacillus thuringiensis
<220> FEATURE:
<221> NAME/KEY: CDS
<222> LOCATION: (1)...(2055)

<400> SEQUENCE: 10 atg gga aat ttt tat ttt gtt atg aag gat aat tac gat tca ctt ata    48
Met Gly Asn Phe Tyr Phe Val Met Lys Asp Asn Tyr Asp Ser Leu Ile
 1               5                  10                  15 aaa aaa gga atg aaa ttt tat atg gat caa tct aat tac gat tat ttg    96
Lys Lys Gly Met Lys Phe Tyr Met Asp Gln Ser Asn Tyr Asp Tyr Leu
            20                  25                  30 tca gat aat gaa aaa caa gaa gtg att ccg aat cca ggg cgc atg ttt   144
Ser Asp Asn Glu Lys Gln Glu Val Ile Pro Asn Pro Gly Arg Met Phe
        35                  40                  45 cat aat tat tca gat aat cct gaa att gca gat tcg caa gag aaa ata   192
His Asn Tyr Ser Asp Asn Pro Glu Ile Ala Asp Ser Gln Glu Lys Ile
```

```
              50                  55                  60
ttt aag att cta aaa aaa gaa aat cta act aaa agt gag caa caa att    240
Phe Lys Ile Leu Lys Lys Glu Asn Leu Thr Lys Ser Glu Gln Gln Ile
 65                  70                  75                  80 ctc gca ggt ata gat ccc aat aat aat gaa gta ggt ccg ttt ctt gtt    288
Leu Ala Gly Ile Asp Pro Asn Asn Asn Glu Val Gly Pro Phe Leu Val
                 85                  90                  95 ccg att atc gcg gca cct atc att ctt act ccg gca atg att cag gtc    336
Pro Ile Ile Ala Ala Pro Ile Ile Leu Thr Pro Ala Met Ile Gln Val
                100                 105                 110 gga caa tgg cta gct gga aaa gca ggg aaa tgg cta att gga aaa gca    384
Gly Gln Trp Leu Ala Gly Lys Ala Gly Lys Trp Leu Ile Gly Lys Ala
            115                 120                 125 ttg ggt aaa tta aaa gga ttt tta ttt cca tca aac aat gat cct gac    432
Leu Gly Lys Leu Lys Gly Phe Leu Phe Pro Ser Asn Asn Asp Pro Asp
130                 135                 140 gct aaa cta gaa gaa atg cgc caa gaa tta gaa gaa caa ttt aat aga    480
Ala Lys Leu Glu Glu Met Arg Gln Glu Leu Glu Glu Gln Phe Asn Arg
145                 150                 155                 160 cgt tta cag aat gat aaa tac caa tca tta ctt gca gct tat gca agt    528
Arg Leu Gln Asn Asp Lys Tyr Gln Ser Leu Leu Ala Ala Tyr Ala Ser
                165                 170                 175 att ttg gat gct gct aat gaa ttt ctt tac tgg gct aat aaa gta gaa    576
Ile Leu Asp Ala Ala Asn Glu Phe Leu Tyr Trp Ala Asn Lys Val Glu
                180                 185                 190 cga gca gaa gaa gct ttt gca aga gat aac tcc gag tca aat aaa aaa    624
Arg Ala Glu Glu Ala Phe Ala Arg Asp Asn Ser Glu Ser Asn Lys Lys
            195                 200                 205 aca tta gaa gac act aaa gcc gac aca gca ggt gca ttt aga gca gta    672
Thr Leu Glu Asp Thr Lys Ala Asp Thr Ala Gly Ala Phe Arg Ala Val
210                 215                 220 aat act gta gca ata agc tgg ata aac cag tgt tta gta cca ggc tat    720
Asn Thr Val Ala Ile Ser Trp Ile Asn Gln Cys Leu Val Pro Gly Tyr
225                 230                 235                 240 gaa gaa att acg tta cct ctt ttc act caa atg tgt act gta cat tta    768
Glu Glu Ile Thr Leu Pro Leu Phe Thr Gln Met Cys Thr Val His Leu
                245                 250                 255 aca cat ttg aaa gat gga gta tta aag gga gcc gat tgg gga ctt gat    816
Thr His Leu Lys Asp Gly Val Leu Lys Gly Ala Asp Trp Gly Leu Asp
                260                 265                 270 cca aaa gac gta gac tcc tat aga tcg ata ttt cat aac aat gtt aac    864
Pro Lys Asp Val Asp Ser Tyr Arg Ser Ile Phe His Asn Asn Val Asn
            275                 280                 285 aaa tat acg caa caa gca atc acc tca ttt cag gca ggt ttc aac cgt    912
Lys Tyr Thr Gln Gln Ala Ile Thr Ser Phe Gln Ala Gly Phe Asn Arg
290                 295                 300 ata gct tct cag aac aac aat act aac tta agt gct gcc tat aat tat    960
Ile Ala Ser Gln Asn Asn Asn Thr Asn Leu Ser Ala Ala Tyr Asn Tyr
305                 310                 315                 320 aga gca gct atg caa gtg tac gca ttt gat tat ata tat aaa tgg tca   1008
Arg Ala Ala Met Gln Val Tyr Ala Phe Asp Tyr Ile Tyr Lys Trp Ser
                325                 330                 335 ttc tta cgc tat gaa gga atc gaa cct gaa gta tct aga acc tta ttt   1056
Phe Leu Arg Tyr Glu Gly Ile Glu Pro Glu Val Ser Arg Thr Leu Phe
                340                 345                 350 tat tct aca gga gtg cca aag ttc cat gaa cct ttt aca cac gag cat   1104
Tyr Ser Thr Gly Val Pro Lys Phe His Glu Pro Phe Thr His Glu His
            355                 360                 365 gtc tat cga acg ctt gtt ggg ctc cca aat act aga atc cga ggg gtg   1152
```

|  |  |
|---|---|
| Val Tyr Arg Thr Leu Val Gly Leu Pro Asn Thr Arg Ile Arg Gly Val<br>    370                                375                        380 | |
| tct gtc gga tac gat gtt agc gct tct aag ata cag tgg cct cta acg<br>Ser Val Gly Tyr Asp Val Ser Ala Ser Lys Ile Gln Trp Pro Leu Thr<br>385                          390                        395                  400 | 1200 |
| ggt gtt aga aac cat gtt tta cct ctc tct gga ggt gat tat cgc gca<br>Gly Val Arg Asn His Val Leu Pro Leu Ser Gly Gly Asp Tyr Arg Ala<br>                       405                        410                        415 | 1248 |
| gaa ttc gga aac tta aat gca gga cta att ggg aac tat act ttt aaa<br>Glu Phe Gly Asn Leu Asn Ala Gly Leu Ile Gly Asn Tyr Thr Phe Lys<br>                  420                        425                      430 | 1296 |
| aca gat cca gct caa tat gaa aaa tct ctt cat ggt caa tta ctg ata<br>Thr Asp Pro Ala Gln Tyr Glu Lys Ser Leu His Gly Gln Leu Leu Ile<br>                435                        440                      445 | 1344 |
| cga tca gac aat ggt aat aca cga tgg att act tac att gat ggt aca<br>Arg Ser Asp Asn Gly Asn Thr Arg Trp Ile Thr Tyr Ile Asp Gly Thr<br>            450                        455                      460 | 1392 |
| ctt ttg gta ggt acc ggt caa ttc acc gga aca gca ttt aat atg cat<br>Leu Leu Val Gly Thr Gly Gln Phe Thr Gly Thr Ala Phe Asn Met His<br>465                          470                        475                  480 | 1440 |
| caa ccg gat cat ttc att cga aca gtt gca gct ata act aaa atg act<br>Gln Pro Asp His Phe Ile Arg Thr Val Ala Ala Ile Thr Lys Met Thr<br>                  485                        490                      495 | 1488 |
| aat aat act tgg tat cct ata att cca ctg aga gga tat cct act ggt<br>Asn Asn Thr Trp Tyr Pro Ile Ile Pro Leu Arg Gly Tyr Pro Thr Gly<br>            500                        505                      510 | 1536 |
| gta gac gca gaa aat atc gtt gca ggt ctt gca cca aat aac gta cag<br>Val Asp Ala Glu Asn Ile Val Ala Gly Leu Ala Pro Asn Asn Val Gln<br>                  515                        520                      525 | 1584 |
| aat ttt atg gca act aat aaa cat aaa att ccg tat gat aaa tcg tat<br>Asn Phe Met Ala Thr Asn Lys His Lys Ile Pro Tyr Asp Lys Ser Tyr<br>530                          535                        540 | 1632 |
| aca atc cca gct ttg cat tat tca aaa atg tca agt gaa aca tct ggt<br>Thr Ile Pro Ala Leu His Tyr Ser Lys Met Ser Ser Glu Thr Ser Gly<br>545                          550                        555                  560 | 1680 |
| aat tca ttt tta tat gat gaa att gca aat ggt gca gat gga gca tta<br>Asn Ser Phe Leu Tyr Asp Glu Ile Ala Asn Gly Ala Asp Gly Ala Leu<br>                  565                        570                      575 | 1728 |
| aga atg aaa cat gga gct act acg gta gat tac aat cta gat ata agt<br>Arg Met Lys His Gly Ala Thr Thr Val Asp Tyr Asn Leu Asp Ile Ser<br>                  580                        585                      590 | 1776 |
| ggg atc aat cgt tca aca aga tat aaa ata ttt att cga gtc aaa gat<br>Gly Ile Asn Arg Ser Thr Arg Tyr Lys Ile Phe Ile Arg Val Lys Asp<br>            595                        600                      605 | 1824 |
| gga agt act ggt ttt gag gtt aaa ctt gtt aat gat cct cgt aca agt<br>Gly Ser Thr Gly Phe Glu Val Lys Leu Val Asn Asp Pro Arg Thr Ser<br>          610                        615                      620 | 1872 |
| ttt aat ttc cat cca att tca agt cat act ggg gaa gcc ggg tat act<br>Phe Asn Phe His Pro Ile Ser Ser His Thr Gly Glu Ala Gly Tyr Thr<br>625                          630                        635                  640 | 1920 |
| gat tat tta tcc gat tca ttt aac ttt tca aat tcc aac gaa atc ctc<br>Asp Tyr Leu Ser Asp Ser Phe Asn Phe Ser Asn Ser Asn Glu Ile Leu<br>                  645                        650                      655 | 1968 |
| aga ata aca cgt aat aac tcc gac act aat gat tta tgg ttt aat cag<br>Arg Ile Thr Arg Asn Asn Ser Asp Thr Asn Asp Leu Trp Phe Asn Gln<br>                  660                        665                      670 | 2016 |
| atc atc ata gtt cta gaa acc act ttt gaa caa tct atg<br>Ile Ile Ile Val Leu Glu Thr Thr Phe Glu Gln Ser Met<br>675                          680                        685 | 2055 |

<210> SEQ ID NO 11
<211> LENGTH: 685
<212> TYPE: PRT
<213> ORGANISM: Bacillus thuringiensis

<400> SEQUENCE: 11

| Met | Gly | Asn | Phe | Tyr | Phe | Val | Met | Lys | Asp | Asn | Tyr | Asp | Ser | Leu | Ile |
|---|---|---|---|---|---|---|---|---|---|---|---|---|---|---|---|
| 1 | | | | 5 | | | | | 10 | | | | | 15 | |
| Lys | Lys | Gly | Met | Lys | Phe | Tyr | Met | Asp | Gln | Ser | Asn | Tyr | Asp | Tyr | Leu |
| | | | 20 | | | | | 25 | | | | | 30 | | |
| Ser | Asp | Asn | Glu | Lys | Gln | Glu | Val | Ile | Pro | Asn | Pro | Gly | Arg | Met | Phe |
| | | 35 | | | | | 40 | | | | | 45 | | | |
| His | Asn | Tyr | Ser | Asp | Asn | Pro | Glu | Ile | Ala | Asp | Ser | Gln | Glu | Lys | Ile |
| | 50 | | | | | 55 | | | | | 60 | | | | |
| Phe | Lys | Ile | Leu | Lys | Lys | Glu | Asn | Leu | Thr | Lys | Ser | Glu | Gln | Gln | Ile |
| 65 | | | | | 70 | | | | | 75 | | | | | 80 |
| Leu | Ala | Gly | Ile | Asp | Pro | Asn | Asn | Glu | Val | Gly | Pro | Phe | Leu | Val |
| | | | | 85 | | | | | 90 | | | | | 95 | |
| Pro | Ile | Ile | Ala | Ala | Pro | Ile | Ile | Leu | Thr | Pro | Ala | Met | Ile | Gln | Val |
| | | | 100 | | | | | 105 | | | | | 110 | | |
| Gly | Gln | Trp | Leu | Ala | Gly | Lys | Ala | Gly | Lys | Trp | Leu | Ile | Gly | Lys | Ala |
| | | 115 | | | | | 120 | | | | | 125 | | | |
| Leu | Gly | Lys | Leu | Lys | Gly | Phe | Leu | Phe | Pro | Ser | Asn | Asn | Asp | Pro | Asp |
| | 130 | | | | | 135 | | | | | 140 | | | | |
| Ala | Lys | Leu | Glu | Glu | Met | Arg | Gln | Glu | Leu | Glu | Glu | Gln | Phe | Asn | Arg |
| 145 | | | | | 150 | | | | | 155 | | | | | 160 |
| Arg | Leu | Gln | Asn | Asp | Lys | Tyr | Gln | Ser | Leu | Leu | Ala | Ala | Tyr | Ala | Ser |
| | | | | 165 | | | | | 170 | | | | | 175 | |
| Ile | Leu | Asp | Ala | Ala | Asn | Glu | Phe | Leu | Tyr | Trp | Ala | Asn | Lys | Val | Glu |
| | | | 180 | | | | | 185 | | | | | 190 | | |
| Arg | Ala | Glu | Glu | Ala | Phe | Ala | Arg | Asp | Asn | Ser | Glu | Ser | Asn | Lys | Lys |
| | | 195 | | | | | 200 | | | | | 205 | | | |
| Thr | Leu | Glu | Asp | Thr | Lys | Ala | Asp | Thr | Ala | Gly | Ala | Phe | Arg | Ala | Val |
| | 210 | | | | | 215 | | | | | 220 | | | | |
| Asn | Thr | Val | Ala | Ile | Ser | Trp | Ile | Asn | Gln | Cys | Leu | Val | Pro | Gly | Tyr |
| 225 | | | | | 230 | | | | | 235 | | | | | 240 |
| Glu | Glu | Ile | Thr | Leu | Pro | Leu | Phe | Thr | Gln | Met | Cys | Thr | Val | His | Leu |
| | | | | 245 | | | | | 250 | | | | | 255 | |
| Thr | His | Leu | Lys | Asp | Gly | Val | Leu | Lys | Gly | Ala | Asp | Trp | Gly | Leu | Asp |
| | | | 260 | | | | | 265 | | | | | 270 | | |
| Pro | Lys | Asp | Val | Asp | Ser | Tyr | Arg | Ser | Ile | Phe | His | Asn | Asn | Val | Asn |
| | | 275 | | | | | 280 | | | | | 285 | | | |
| Lys | Tyr | Thr | Gln | Gln | Ala | Ile | Thr | Ser | Phe | Gln | Ala | Gly | Phe | Asn | Arg |
| | 290 | | | | | 295 | | | | | 300 | | | | |
| Ile | Ala | Ser | Gln | Asn | Asn | Thr | Asn | Leu | Ser | Ala | Ala | Tyr | Asn | Tyr |
| 305 | | | | | 310 | | | | | 315 | | | | | 320 |
| Arg | Ala | Ala | Met | Gln | Val | Tyr | Ala | Phe | Asp | Tyr | Ile | Tyr | Lys | Trp | Ser |
| | | | | 325 | | | | | 330 | | | | | 335 | |
| Phe | Leu | Arg | Tyr | Glu | Gly | Ile | Glu | Pro | Glu | Val | Ser | Arg | Thr | Leu | Phe |
| | | | 340 | | | | | 345 | | | | | 350 | | |
| Tyr | Ser | Thr | Gly | Val | Pro | Lys | Phe | His | Glu | Pro | Phe | Thr | His | Glu | His |
| | | 355 | | | | | 360 | | | | | 365 | | | |
| Val | Tyr | Arg | Thr | Leu | Val | Gly | Leu | Pro | Asn | Thr | Arg | Ile | Arg | Gly | Val |
| | 370 | | | | | 375 | | | | | 380 | | | | |

-continued

```
Ser Val Gly Tyr Asp Val Ser Ala Ser Lys Ile Gln Trp Pro Leu Thr
385                 390                 395                 400

Gly Val Arg Asn His Val Leu Pro Leu Ser Gly Gly Asp Tyr Arg Ala
                405                 410                 415

Glu Phe Gly Asn Leu Asn Ala Gly Leu Ile Gly Asn Tyr Thr Phe Lys
            420                 425                 430

Thr Asp Pro Ala Gln Tyr Glu Lys Ser Leu His Gly Gln Leu Leu Ile
        435                 440                 445

Arg Ser Asp Asn Gly Asn Thr Arg Trp Ile Thr Tyr Ile Asp Gly Thr
    450                 455                 460

Leu Leu Val Gly Thr Gly Gln Phe Thr Gly Thr Ala Phe Asn Met His
465                 470                 475                 480

Gln Pro Asp His Phe Ile Arg Thr Val Ala Ala Ile Thr Lys Met Thr
                485                 490                 495

Asn Asn Thr Trp Tyr Pro Ile Ile Pro Leu Arg Gly Tyr Pro Thr Gly
            500                 505                 510

Val Asp Ala Glu Asn Ile Val Ala Gly Leu Ala Pro Asn Asn Val Gln
        515                 520                 525

Asn Phe Met Ala Thr Asn Lys His Lys Ile Pro Tyr Asp Lys Ser Tyr
    530                 535                 540

Thr Ile Pro Ala Leu His Tyr Ser Lys Met Ser Ser Glu Thr Ser Gly
545                 550                 555                 560

Asn Ser Phe Leu Tyr Asp Glu Ile Ala Asn Gly Ala Asp Gly Ala Leu
                565                 570                 575

Arg Met Lys His Gly Ala Thr Thr Val Asp Tyr Asn Leu Asp Ile Ser
            580                 585                 590

Gly Ile Asn Arg Ser Thr Arg Tyr Lys Ile Phe Ile Arg Val Lys Asp
        595                 600                 605

Gly Ser Thr Gly Phe Glu Val Lys Leu Val Asn Asp Pro Arg Thr Ser
    610                 615                 620

Phe Asn Phe His Pro Ile Ser Ser His Thr Gly Glu Ala Gly Tyr Thr
625                 630                 635                 640

Asp Tyr Leu Ser Asp Ser Phe Asn Phe Ser Asn Ser Asn Glu Ile Leu
                645                 650                 655

Arg Ile Thr Arg Asn Asn Ser Asp Thr Asn Asp Leu Trp Phe Asn Gln
            660                 665                 670

Ile Ile Ile Val Leu Glu Thr Thr Phe Glu Gln Ser Met
        675                 680                 685
```

<210> SEQ ID NO 12
<211> LENGTH: 2151
<212> TYPE: DNA
<213> ORGANISM: Paenibacillus popilliae
<220> FEATURE:
<221> NAME/KEY: CDS
<222> LOCATION: (1)...(2151)

<400> SEQUENCE: 12

```
atg ctg gaa tgc tct gag gcg atg ggg atc gat ttg aat gct cct aat       48
Met Leu Glu Cys Ser Glu Ala Met Gly Ile Asp Leu Asn Ala Pro Asn
 1               5                  10                  15 att agg gag gct ctt agt atg aac aat tac ttt att gga aaa gtt cta       96
Ile Arg Glu Ala Leu Ser Met Asn Asn Tyr Phe Ile Gly Lys Val Leu
            20                  25                  30 agc gga cat cat ata aac aat aac ggt aat gga aat acg cta agc aga      144
Ser Gly His His Ile Asn Asn Asn Gly Asn Gly Asn Thr Leu Ser Arg

|  |  |
|---|---|
| acg gct tta act cct aca aat aac aat gtt aat cgt ggt gat tta gtt<br>Thr Ala Leu Thr Pro Thr Asn Asn Asn Val Asn Arg Gly Asp Leu Val<br>50                     55                    60 | 192 |
| acg aat ggt tta act cca ata gat aac aat ttt ata ggt agt aat ggt<br>Thr Asn Gly Leu Thr Pro Ile Asp Asn Asn Phe Ile Gly Ser Asn Gly<br>65                    70                    75                  80 | 240 |
| ttt att ccc aga aat gta acg aga aaa gat cct ttt cgc aag aga aca<br>Phe Ile Pro Arg Asn Val Thr Arg Lys Asp Pro Phe Arg Lys Arg Thr<br>                85                    90                    95 | 288 |
| aca caa gaa ttc ata agg gaa tgg aca gaa tgg aaa gaa aaa agt gct<br>Thr Gln Glu Phe Ile Arg Glu Trp Thr Glu Trp Lys Glu Lys Ser Ala<br>          100                    105               110 | 336 |
| tct ttg ttt aca gca cca att gta ggt gtt att acc agt act ctt ctt<br>Ser Leu Phe Thr Ala Pro Ile Val Gly Val Ile Thr Ser Thr Leu Leu<br>          115                    120               125 | 384 |
| gaa gca tta aaa aaa cta gta gcg ggc aga gtt tta atg tca ttg aca<br>Glu Ala Leu Lys Lys Leu Val Ala Gly Arg Val Leu Met Ser Leu Thr<br>130                     135                    140 | 432 |
| aac ctt tta ttt cct aac aac agt aca tca acg atg gaa gaa att tta<br>Asn Leu Leu Phe Pro Asn Asn Ser Thr Ser Thr Met Glu Glu Ile Leu<br>145                     150                    155               160 | 480 |
| cga gct aca gaa caa tat att cag gaa cag ctt gat act gta acc tgg<br>Arg Ala Thr Glu Gln Tyr Ile Gln Glu Gln Leu Asp Thr Val Thr Trp<br>                 165                    170               175 | 528 |
| aat cgt gtg tca cag gaa ctg gaa ggt ttg aag aat gac cta cga acc<br>Asn Arg Val Ser Gln Glu Leu Glu Gly Leu Lys Asn Asp Leu Arg Thr<br>          180                    185               190 | 576 |
| ttt aac gat caa atc gat gat ttt tta caa aat aga gtg ggg att tca<br>Phe Asn Asp Gln Ile Asp Asp Phe Leu Gln Asn Arg Val Gly Ile Ser<br>                195                    200               205 | 624 |
| cca ctt gca atc ata gat tcg att aat acc atg caa cag tta ttt gtg<br>Pro Leu Ala Ile Ile Asp Ser Ile Asn Thr Met Gln Gln Leu Phe Val<br>210                     215                    220 | 672 |
| aat aga ttg cca cag ttc caa gta agc gac gat caa gta tta tta tta<br>Asn Arg Leu Pro Gln Phe Gln Val Ser Asp Asp Gln Val Leu Leu Leu<br>225                     230                    235               240 | 720 |
| cct tta ttt gca caa gca gtc acg cta cat tta act ttt gta cgg gat<br>Pro Leu Phe Ala Gln Ala Val Thr Leu His Leu Thr Phe Val Arg Asp<br>                 245                    250               255 | 768 |
| att atc att aat gct gat gaa tgg aat att ccc gaa gct caa ttg aac<br>Ile Ile Ile Asn Ala Asp Glu Trp Asn Ile Pro Glu Ala Gln Leu Asn<br>          260                    265               270 | 816 |
| acg tat aag cga tat ctt aaa caa tat gta gca caa tat tcc aat tat<br>Thr Tyr Lys Arg Tyr Leu Lys Gln Tyr Val Ala Gln Tyr Ser Asn Tyr<br>          275                    280               285 | 864 |
| gct tta tcc acc tat gag gag gca ttt aga gca aga ttt tat cca aga<br>Ala Leu Ser Thr Tyr Glu Glu Ala Phe Arg Ala Arg Phe Tyr Pro Arg<br>290                     295                    300 | 912 |
| aat acg gta gag aac atg cta caa ttt aaa acg ttt atg aca ata aat<br>Asn Thr Val Glu Asn Met Leu Gln Phe Lys Thr Phe Met Thr Ile Asn<br>305                     310                    315               320 | 960 |
| gta cta gat ttt gtt tca att tgg tca ttg ctt aaa tat gta aac cta<br>Val Leu Asp Phe Val Ser Ile Trp Ser Leu Leu Lys Tyr Val Asn Leu<br>                 325                    330               335 | 1008 |
| tat gta agc aca agt gca aat tta tat aat ata ggc gat aat aag gtg<br>Tyr Val Ser Thr Ser Ala Asn Leu Tyr Asn Ile Gly Asp Asn Lys Val<br>          340                    345               350 | 1056 |
| aat gag ggg gaa tat tcg atc tcc tat tgg ccg ttc ttt aac tct tat | 1104 |

```
                Asn Glu Gly Glu Tyr Ser Ile Ser Tyr Trp Pro Phe Phe Asn Ser Tyr
                            355                 360                 365 att cag aca aga gcg aat tat gta ttg tct ggt gta tca ggg tat gcc        1152
Ile Gln Thr Arg Ala Asn Tyr Val Leu Ser Gly Val Ser Gly Tyr Ala
        370                 375                 380 ata cgt tgg act tat aat aat cct atc ttt gga cga tac att caa gat        1200
Ile Arg Trp Thr Tyr Asn Asn Pro Ile Phe Gly Arg Tyr Ile Gln Asp
385                 390                 395                 400 aga ctt aat aat att acc gcc tct tat atc ggt ggg gta aat gga cca        1248
Arg Leu Asn Asn Ile Thr Ala Ser Tyr Ile Gly Gly Val Asn Gly Pro
                405                 410                 415 caa att ggc caa cag ctt tct aca acc gaa ctc gat caa cta gta caa        1296
Gln Ile Gly Gln Gln Leu Ser Thr Thr Glu Leu Asp Gln Leu Val Gln
        420                 425                 430 caa caa gct aga gct gat ata cca gta gac ttt acg cag atc cca atc        1344
Gln Gln Ala Arg Ala Asp Ile Pro Val Asp Phe Thr Gln Ile Pro Ile
            435                 440                 445 aat tgt aca cta cga aat ccg tta gaa gta ccc tat tat gct act cga        1392
Asn Cys Thr Leu Arg Asn Pro Leu Glu Val Pro Tyr Tyr Ala Thr Arg
        450                 455                 460 ttc aat gaa tta act tca ttg ggg aca gcg gga gtt ggc gga ttc gtt        1440
Phe Asn Glu Leu Thr Ser Leu Gly Thr Ala Gly Val Gly Gly Phe Val
465                 470                 475                 480 cgt agt gac gtc ttt ata agt aat gat agt gtg tgc ggt ctt gga acc        1488
Arg Ser Asp Val Phe Ile Ser Asn Asp Ser Val Cys Gly Leu Gly Thr
                485                 490                 495 aac tat tct agt ggt cag aca ttt tat cca gat tat tat att aca aat        1536
Asn Tyr Ser Ser Gly Gln Thr Phe Tyr Pro Asp Tyr Tyr Ile Thr Asn
            500                 505                 510 att tct gca act gta caa gta aac gga aca aat aca gat ata agt ccg        1584
Ile Ser Ala Thr Val Gln Val Asn Gly Thr Asn Thr Asp Ile Ser Pro
        515                 520                 525 tta tat ttt gga gaa aat aga gcc ata act tct act aat ggt gta aat        1632
Leu Tyr Phe Gly Glu Asn Arg Ala Ile Thr Ser Thr Asn Gly Val Asn
    530                 535                 540 aaa gtg atc gct att tat aat agg aaa acc aat tat gat gat ttt aca        1680
Lys Val Ile Ala Ile Tyr Asn Arg Lys Thr Asn Tyr Asp Asp Phe Thr
545                 550                 555                 560 aat ata cgt ggt acc ata gtc cat gaa gca cct aca gat agt acc ggt        1728
Asn Ile Arg Gly Thr Ile Val His Glu Ala Pro Thr Asp Ser Thr Gly
                565                 570                 575 ttt act ata tct cca ttg cat ctg gat aca gtc aac atc aat tca tat        1776
Phe Thr Ile Ser Pro Leu His Leu Asp Thr Val Asn Ile Asn Ser Tyr
            580                 585                 590 ttg tat att caa gaa aat tat ggg aat aat ggt gat tca ctg cga gta        1824
Leu Tyr Ile Gln Glu Asn Tyr Gly Asn Asn Gly Asp Ser Leu Arg Val
        595                 600                 605 att aac agg gct ata ata aag tat aga ctt agc gca gct cgt tca gtt        1872
Ile Asn Arg Ala Ile Ile Lys Tyr Arg Leu Ser Ala Ala Arg Ser Val
    610                 615                 620 ata tac aga tta gtt tta aga gta tct gga act gca tca agt ata gtt        1920
Ile Tyr Arg Leu Val Leu Arg Val Ser Gly Thr Ala Ser Ser Ile Val
625                 630                 635                 640 gca ata tat gag aat tat cct gta gga tca gca aat cag atc aat aca        1968
Ala Ile Tyr Glu Asn Tyr Pro Val Gly Ser Ala Asn Gln Ile Asn Thr
                645                 650                 655 ggt act gac aac gaa gga gtt ata gac aat gat tca aaa ttt ata gat        2016
Gly Thr Asp Asn Glu Gly Val Ile Asp Asn Asp Ser Lys Phe Ile Asp
            660                 665                 670
```

-continued

```
tta att ttt aat acg cct ttt tct gta tca gga acg gcg aga gaa ttg      2064
Leu Ile Phe Asn Thr Pro Phe Ser Val Ser Gly Thr Ala Arg Glu Leu
            675                 680                 685 cag tta caa gtt tcc ggg gca act aca tct agt ccc ctt gat ata atg      2112
Gln Leu Gln Val Ser Gly Ala Thr Thr Ser Ser Pro Leu Asp Ile Met
690                 695                 700 aat atc atc ttg att cca ata aat gat gtt cct ctt tat                  2151
Asn Ile Ile Leu Ile Pro Ile Asn Asp Val Pro Leu Tyr
705                 710                 715
```

<210> SEQ ID NO 13
<211> LENGTH: 717
<212> TYPE: PRT
<213> ORGANISM: Paenibacillus popilliae

<400> SEQUENCE: 13

```
Met Leu Glu Cys Ser Glu Ala Met Gly Ile Asp Leu Asn Ala Pro Asn
1               5                   10                  15

Ile Arg Glu Ala Leu Ser Met Asn Asn Tyr Phe Ile Gly Lys Val Leu
            20                  25                  30

Ser Gly His His Ile Asn Asn Asn Gly Asn Gly Asn Thr Leu Ser Arg
        35                  40                  45

Thr Ala Leu Thr Pro Thr Asn Asn Val Asn Arg Gly Asp Leu Val
    50                  55                  60

Thr Asn Gly Leu Thr Pro Ile Asp Asn Asn Phe Ile Gly Ser Asn Gly
65                  70                  75                  80

Phe Ile Pro Arg Asn Val Thr Arg Lys Asp Pro Phe Arg Lys Arg Thr
                85                  90                  95

Thr Gln Glu Phe Ile Arg Glu Trp Thr Glu Trp Lys Glu Lys Ser Ala
            100                 105                 110

Ser Leu Phe Thr Ala Pro Ile Val Gly Val Ile Thr Ser Thr Leu Leu
        115                 120                 125

Glu Ala Leu Lys Lys Leu Val Ala Gly Arg Val Leu Met Ser Leu Thr
    130                 135                 140

Asn Leu Leu Phe Pro Asn Asn Ser Thr Ser Thr Met Glu Glu Ile Leu
145                 150                 155                 160

Arg Ala Thr Glu Gln Tyr Ile Gln Glu Gln Leu Asp Thr Val Thr Trp
                165                 170                 175

Asn Arg Val Ser Gln Glu Leu Glu Gly Leu Lys Asn Asp Leu Arg Thr
            180                 185                 190

Phe Asn Asp Gln Ile Asp Asp Phe Leu Gln Asn Arg Val Gly Ile Ser
        195                 200                 205

Pro Leu Ala Ile Ile Asp Ser Ile Asn Thr Met Gln Gln Leu Phe Val
    210                 215                 220

Asn Arg Leu Pro Gln Phe Gln Val Ser Asp Asp Gln Val Leu Leu Leu
225                 230                 235                 240

Pro Leu Phe Ala Gln Ala Val Thr Leu His Leu Thr Phe Val Arg Asp
                245                 250                 255

Ile Ile Ile Asn Ala Asp Glu Trp Asn Ile Pro Glu Ala Gln Leu Asn
            260                 265                 270

Thr Tyr Lys Arg Tyr Leu Lys Gln Tyr Val Ala Gln Tyr Ser Asn Tyr
        275                 280                 285

Ala Leu Ser Thr Tyr Glu Glu Ala Phe Arg Ala Arg Phe Tyr Pro Arg
    290                 295                 300

Asn Thr Val Glu Asn Met Leu Gln Phe Lys Thr Phe Met Thr Ile Asn
305                 310                 315                 320
```

```
Val Leu Asp Phe Val Ser Ile Trp Ser Leu Leu Lys Tyr Val Asn Leu
                325                 330                 335

Tyr Val Ser Thr Ser Ala Asn Leu Tyr Asn Ile Gly Asp Asn Lys Val
            340                 345                 350

Asn Glu Gly Glu Tyr Ser Ile Ser Tyr Trp Pro Phe Phe Asn Ser Tyr
        355                 360                 365

Ile Gln Thr Arg Ala Asn Tyr Val Leu Ser Gly Val Ser Gly Tyr Ala
    370                 375                 380

Ile Arg Trp Thr Tyr Asn Asn Pro Ile Phe Gly Arg Tyr Ile Gln Asp
385                 390                 395                 400

Arg Leu Asn Asn Ile Thr Ala Ser Tyr Ile Gly Gly Val Asn Gly Pro
                405                 410                 415

Gln Ile Gly Gln Leu Ser Thr Thr Glu Leu Asp Gln Leu Val Gln
            420                 425                 430

Gln Gln Ala Arg Ala Asp Ile Pro Val Asp Phe Thr Gln Ile Pro Ile
        435                 440                 445

Asn Cys Thr Leu Arg Asn Pro Leu Glu Val Pro Tyr Tyr Ala Thr Arg
    450                 455                 460

Phe Asn Glu Leu Thr Ser Leu Gly Thr Ala Gly Val Gly Gly Phe Val
465                 470                 475                 480

Arg Ser Asp Val Phe Ile Ser Asn Asp Ser Val Cys Gly Leu Gly Thr
                485                 490                 495

Asn Tyr Ser Ser Gly Gln Thr Phe Tyr Pro Asp Tyr Tyr Ile Thr Asn
            500                 505                 510

Ile Ser Ala Thr Val Gln Val Asn Gly Thr Asn Thr Asp Ile Ser Pro
        515                 520                 525

Leu Tyr Phe Gly Glu Asn Arg Ala Ile Thr Ser Thr Asn Gly Val Asn
    530                 535                 540

Lys Val Ile Ala Ile Tyr Asn Arg Lys Thr Asn Tyr Asp Asp Phe Thr
545                 550                 555                 560

Asn Ile Arg Gly Thr Ile Val His Glu Ala Pro Thr Asp Ser Thr Gly
                565                 570                 575

Phe Thr Ile Ser Pro Leu His Leu Asp Thr Val Asn Ile Asn Ser Tyr
            580                 585                 590

Leu Tyr Ile Gln Glu Asn Tyr Gly Asn Asn Gly Asp Ser Leu Arg Val
        595                 600                 605

Ile Asn Arg Ala Ile Ile Lys Tyr Arg Leu Ser Ala Ala Arg Ser Val
    610                 615                 620

Ile Tyr Arg Leu Val Leu Arg Val Ser Gly Thr Ala Ser Ser Ile Val
625                 630                 635                 640

Ala Ile Tyr Glu Asn Tyr Pro Val Gly Ser Ala Asn Gln Ile Asn Thr
                645                 650                 655

Gly Thr Asp Asn Glu Gly Val Ile Asp Asn Asp Ser Lys Phe Ile Asp
            660                 665                 670

Leu Ile Phe Asn Thr Pro Phe Ser Val Ser Gly Thr Ala Arg Glu Leu
    675                 680                 685

Gln Leu Gln Val Ser Gly Ala Thr Thr Ser Ser Pro Leu Asp Ile Met
690                 695                 700

Asn Ile Ile Leu Ile Pro Ile Asn Asp Val Pro Leu Tyr
705                 710                 715

<210> SEQ ID NO 14
<211> LENGTH: 643
```

<212> TYPE: PRT
<213> ORGANISM: Bacillus thuringiensis

<400> SEQUENCE: 14

```
Met Glu Asp Ser Ser Leu Asp Thr Leu Ser Ile Val Asn Glu Thr Asp
 1               5                  10                  15

Phe Pro Leu Tyr Asn Asn Tyr Thr Glu Pro Thr Ile Ala Pro Ala Leu
             20                  25                  30

Ile Ala Val Ala Pro Ile Ala Gln Tyr Leu Ala Thr Ala Ile Gly Lys
         35                  40                  45

Trp Ala Ala Lys Ala Ala Phe Ser Lys Val Leu Ser Leu Ile Phe Pro
 50                  55                  60

Gly Ser Gln Pro Ala Thr Met Glu Lys Val Arg Thr Glu Val Glu Thr
 65                  70                  75                  80

Leu Ile Asn Gln Lys Leu Ser Gln Asp Arg Val Asn Ile Leu Asn Ala
                 85                  90                  95

Glu Tyr Arg Gly Ile Ile Glu Val Ser Asp Val Phe Asp Ala Tyr Ile
            100                 105                 110

Lys Gln Pro Gly Phe Thr Pro Ala Thr Ala Lys Gly Tyr Phe Leu Asn
        115                 120                 125

Leu Ser Gly Ala Ile Ile Gln Arg Leu Pro Gln Phe Glu Val Gln Thr
130                 135                 140

Tyr Glu Gly Val Ser Ile Ala Leu Phe Thr Gln Met Cys Thr Leu His
145                 150                 155                 160

Leu Thr Leu Leu Lys Asp Gly Ile Leu Ala Gly Ser Ala Trp Gly Phe
                165                 170                 175

Thr Gln Ala Asp Val Asp Ser Phe Ile Lys Leu Phe Asn Gln Lys Val
            180                 185                 190

Leu Asp Tyr Arg Thr Arg Leu Met Arg Met Tyr Thr Glu Glu Phe Gly
        195                 200                 205

Arg Leu Cys Lys Val Ser Leu Lys Asp Gly Leu Thr Phe Arg Asn Met
210                 215                 220

Cys Asn Leu Tyr Val Phe Pro Phe Ala Glu Ala Trp Ser Leu Met Arg
225                 230                 235                 240

Tyr Glu Gly Leu Lys Leu Gln Ser Ser Leu Ser Leu Trp Asp Tyr Val
                245                 250                 255

Gly Val Ser Ile Pro Val Asn Tyr Asn Glu Trp Gly Gly Leu Val Tyr
            260                 265                 270

Lys Leu Leu Met Gly Glu Val Asn Gln Arg Leu Thr Thr Val Lys Phe
        275                 280                 285

Asn Tyr Ser Phe Thr Asn Glu Pro Ala Asp Ile Pro Ala Arg Glu Asn
290                 295                 300

Ile Arg Gly Val His Pro Ile Tyr Asp Pro Ser Ser Gly Leu Thr Gly
305                 310                 315                 320

Trp Ile Gly Asn Gly Arg Thr Asn Asn Phe Asn Ala Asp Asn Asn
                325                 330                 335

Gly Asn Glu Ile Met Glu Val Arg Thr Gln Thr Phe Tyr Gln Asn Pro
            340                 345                 350

Asn Asn Glu Pro Ile Ala Pro Arg Asp Ile Ile Asn Gln Ile Leu Thr
        355                 360                 365

Ala Pro Ala Pro Ala Asp Leu Phe Lys Asn Ala Asp Ile Asn Val
370                 375                 380

Lys Phe Thr Gln Trp Phe Gln Ser Thr Leu Tyr Gly Trp Asn Ile Lys
385                 390                 395                 400
```

```
Leu Gly Thr Gln Thr Val Leu Ser Ser Arg Thr Gly Thr Ile Pro Pro
                405                 410                 415

Asn Tyr Leu Ala Tyr Asp Gly Tyr Tyr Ile Arg Ala Ile Ser Ala Cys
            420                 425                 430

Pro Arg Gly Val Ser Leu Ala Tyr Asn His Asp Leu Thr Thr Leu Thr
        435                 440                 445

Tyr Asn Arg Ile Glu Tyr Asp Ser Pro Thr Thr Glu Asn Ile Ile Val
    450                 455                 460

Gly Phe Ala Pro Asp Asn Thr Lys Asp Phe Tyr Ser Lys Lys Ser His
465                 470                 475                 480

Tyr Leu Ser Glu Thr Asn Asp Ser Tyr Val Ile Pro Ala Leu Gln Phe
                485                 490                 495

Ala Glu Val Ser Asp Arg Ser Phe Leu Glu Asp Thr Pro Asp Gln Ala
            500                 505                 510

Thr Asp Gly Ser Ile Lys Phe Ala Arg Thr Phe Ile Ser Asn Glu Ala
        515                 520                 525

Lys Tyr Ser Ile Arg Leu Asn Thr Gly Phe Asn Thr Ala Thr Arg Tyr
    530                 535                 540

Lys Leu Ile Ile Arg Val Arg Val Pro Tyr Arg Leu Pro Ala Gly Ile
545                 550                 555                 560

Arg Val Gln Ser Gln Asn Ser Gly Asn Asn Arg Met Leu Gly Ser Phe
                565                 570                 575

Thr Ala Asn Ala Asn Pro Glu Trp Val Asp Phe Val Thr Asp Ala Phe
            580                 585                 590

Thr Phe Asn Asp Leu Gly Ile Thr Thr Ser Ser Thr Asn Ala Leu Phe
        595                 600                 605

Ser Ile Ser Ser Asp Ser Leu Asn Ser Gly Glu Glu Trp Tyr Leu Ser
    610                 615                 620

Gln Leu Phe Leu Val Lys Glu Ser Ala Phe Thr Thr Gln Ile Asn Pro
625                 630                 635                 640

Leu Leu Lys

<210> SEQ ID NO 15
<211> LENGTH: 724
<212> TYPE: PRT
<213> ORGANISM: Bacillus thuringiensis

<400> SEQUENCE: 15

Met Gln Asn Asn Asn Phe Asn Thr Thr Glu Ile Asn Asn Met Ile Asn
 1               5                  10                  15

Phe Pro Met Tyr Asn Gly Arg Leu Glu Pro Ser Leu Ala Pro Ala Leu
            20                  25                  30

Ile Ala Val Ala Pro Ile Ala Lys Tyr Leu Ala Thr Ala Leu Ala Lys
        35                  40                  45

Trp Ala Val Lys Gln Gly Phe Ala Lys Leu Lys Ser Glu Ile Phe Pro
    50                  55                  60

Gly Asn Thr Pro Ala Thr Met Asp Lys Val Arg Ile Glu Val Gln Thr
65                  70                  75                  80

Leu Leu Asp Gln Arg Leu Gln Asp Asp Arg Val Lys Ile Leu Glu Gly
                85                  90                  95

Glu Tyr Lys Gly Ile Ile Asp Val Ser Lys Val Phe Thr Asp Tyr Val
            100                 105                 110

Asn Gln Ser Lys Phe Glu Thr Gly Thr Ala Asn Arg Leu Phe Phe Asp
        115                 120                 125
```

```
Thr Ser Asn Gln Leu Ile Ser Arg Leu Pro Gln Phe Glu Ile Ala Gly
    130                 135                 140

Tyr Glu Gly Val Ser Ile Ser Leu Phe Thr Gln Met Cys Thr Phe His
145                 150                 155                 160

Leu Gly Leu Leu Lys Asp Gly Ile Leu Ala Gly Ser Asp Trp Gly Phe
                165                 170                 175

Ala Pro Ala Asp Lys Asp Ala Leu Ile Cys Gln Phe Asn Arg Phe Val
            180                 185                 190

Asn Glu Tyr Asn Thr Arg Leu Met Val Leu Tyr Ser Lys Glu Phe Gly
        195                 200                 205

Arg Leu Leu Ala Lys Asn Leu Asn Glu Ala Leu Asn Phe Arg Asn Met
210                 215                 220

Cys Ser Leu Tyr Val Phe Pro Phe Ser Glu Ala Trp Ser Leu Leu Arg
225                 230                 235                 240

Tyr Glu Gly Thr Lys Leu Glu Asn Thr Leu Ser Leu Trp Asn Phe Val
                245                 250                 255

Gly Glu Ser Ile Asn Asn Ile Ser Pro Asn Asp Trp Lys Gly Ala Leu
            260                 265                 270

Tyr Lys Leu Leu Met Gly Ala Pro Asn Gln Arg Leu Asn Asn Val Lys
        275                 280                 285

Phe Asn Tyr Ser Tyr Phe Ser Asp Thr Gln Ala Thr Ile His Arg Glu
290                 295                 300

Asn Ile His Gly Val Leu Pro Thr Tyr Asn Gly Gly Pro Thr Ile Thr
305                 310                 315                 320

Gly Trp Ile Gly Asn Gly Arg Phe Ser Gly Leu Ser Phe Pro Cys Ser
                325                 330                 335

Asn Glu Leu Glu Ile Thr Lys Ile Lys Gln Glu Ile Thr Tyr Asn Asp
            340                 345                 350

Lys Gly Gly Asn Phe Asn Ser Ile Val Pro Ala Ala Thr Arg Asn Glu
        355                 360                 365

Ile Leu Thr Ala Thr Val Pro Thr Ser Ala Asp Pro Phe Phe Lys Thr
370                 375                 380

Ala Asp Ile Asn Trp Lys Tyr Phe Ser Pro Gly Leu Tyr Ser Gly Trp
385                 390                 395                 400

Asn Ile Lys Phe Asp Asp Thr Val Thr Leu Lys Ser Arg Val Pro Ser
                405                 410                 415

Ile Ile Pro Ser Asn Ile Leu Lys Tyr Asp Asp Tyr Tyr Ile Arg Ala
            420                 425                 430

Val Ser Ala Cys Pro Lys Gly Val Ser Leu Ala Tyr Asn His Asp Phe
        435                 440                 445

Leu Thr Leu Thr Tyr Asn Lys Leu Glu Tyr Asp Ala Pro Thr Thr Gln
450                 455                 460

Asn Ile Ile Val Gly Phe Ser Pro Asp Asn Thr Lys Ser Phe Tyr Arg
465                 470                 475                 480

Ser Asn Ser His Tyr Leu Ser Thr Thr Asp Asp Ala Tyr Val Ile Pro
                485                 490                 495

Ala Leu Gln Phe Ser Thr Val Ser Asp Arg Ser Phe Leu Glu Asp Thr
            500                 505                 510

Pro Asp Gln Ala Thr Asp Gly Ser Ile Lys Phe Thr Asp Thr Val Leu
        515                 520                 525

Gly Asn Glu Ala Lys Tyr Ser Ile Arg Leu Asn Thr Gly Phe Asn Thr
530                 535                 540
```

-continued

```
Ala Thr Arg Tyr Arg Leu Ile Ile Arg Phe Lys Ala Pro Ala Arg Leu
545                 550                 555                 560

Ala Ala Gly Ile Arg Val Arg Ser Gln Asn Ser Gly Asn Asn Lys Leu
                565                 570                 575

Leu Gly Gly Ile Pro Val Glu Gly Asn Ser Gly Trp Ile Asp Tyr Ile
            580                 585                 590

Thr Asp Ser Phe Thr Phe Asp Asp Leu Gly Ile Thr Thr Ser Ser Thr
        595                 600                 605

Asn Ala Phe Phe Ser Ile Asp Ser Asp Gly Val Asn Ala Ser Gln Gln
    610                 615                 620

Trp Tyr Leu Ser Lys Leu Ile Leu Val Lys Glu Ser Ser Phe Thr Thr
625                 630                 635                 640

Gln Ile Pro Leu Lys Pro Tyr Val Ile Val Arg Cys Pro Asp Thr Phe
                645                 650                 655

Phe Val Ser Asn Asn Ser Ser Ser Thr Tyr Glu Gln Gly Tyr Asn Asn
            660                 665                 670

Asn Tyr Asn Gln Asn Ser Ser Ser Met Tyr Asp Gln Gly Tyr Asn Asn
        675                 680                 685

Ser Tyr Asn Pro Asn Ser Gly Cys Thr Cys Asn Gln Asp Tyr Asn Asn
    690                 695                 700

Ser Tyr Asn Gln Asn Ser Gly Cys Thr Cys Asn Gln Gly Tyr Asn Asn
705                 710                 715                 720

Asn Tyr Pro Lys
```